United States Patent
Nishimori et al.

(10) Patent No.: US 8,853,359 B2
(45) Date of Patent: Oct. 7, 2014

(54) ENDOKININ C/D-DERIVED PEPTIDES

(75) Inventors: Toshikazu Nishimori, Miyazaki (JP); Rumi Naono, Miyazaki (JP)

(73) Assignee: University of Miyazaki, Miyazaki-Shi (Miyazaki) (JP)

( * ) Notice: Subject to any disclaimer, the term of this patent is extended or adjusted under 35 U.S.C. 154(b) by 193 days.

(21) Appl. No.: 13/375,668

(22) PCT Filed: May 31, 2010

(86) PCT No.: PCT/JP2010/059203
§ 371 (c)(1),
(2), (4) Date: Dec. 1, 2011

(87) PCT Pub. No.: WO2010/140567
PCT Pub. Date: Dec. 9, 2010

(65) Prior Publication Data
US 2012/0094911 A1    Apr. 19, 2012

(30) Foreign Application Priority Data

Jun. 2, 2009 (JP) ................................. 2009-133339

(51) Int. Cl.
*A61K 38/08* (2006.01)
*A61K 38/10* (2006.01)
*C07K 7/08* (2006.01)
*C07K 7/06* (2006.01)
*A61K 38/00* (2006.01)

(52) U.S. Cl.
CPC ... *C07K 7/06* (2013.01); *C07K 7/08* (2013.01); *A61K 38/00* (2013.01)
USPC ........ 530/327; 514/12.2; 514/18.3; 514/21.5; 514/21.6

(58) Field of Classification Search
CPC .............. C07K 7/22; C07K 7/06; C07K 7/08; A61K 38/00
See application file for complete search history.

(56) References Cited

U.S. PATENT DOCUMENTS 7,235,531 B2 * 6/2007 Itoh et al. ...................... 514/15.7
2004/0216190 A1* 10/2004 Kovalic ........................ 800/289

OTHER PUBLICATIONS

Brueggemann et al. "The complete genome sequence of Propionibacterium acnes, a commensal of human skin", Science, pp. 671-673, 2004.*
Caplus citation Answer 6 of 13; obtained Aug. 10, 2013; p. 1 for Brueggemann et al. "The complete genome sequence of Propionibacterium acnes, a commensal of human skin", Science, pp. 671-673, 2004.*
Caplus citation Answer 5 of 13, obtained Aug. 10, 2013 for Kovalic, US 20040216190 A1; published 2004, pp. 1-2.*
Andoh et al., "Substance P Induction of Itch-Associated Response Mediated by Cutaneous NK1 Tachykinin Receptors in Mice", The Journal of Pharmacology and Experimental Therapeutics, 1998, pp. 1140-1145.*
Zheng et al.,"Differential roles of spinal neurokinin ½ receptors in development of persistent spontaneous nociception and hyperalgesia induced by subcutaneous bee venom injection in the conscious rat", Neuropeptides, 2001, pp. 32-44.*
Mitsuhiko et al., "Pharmacological profile of a tachykinin antagonist, spantide, as examined on rat spinal motoneurones", Br. J. Pharmacol., 1990, pp. 711-716.*
Rumi Naono-Nakayama, et al: "Pharmacological characteristics of endokinin C/D-derived peptides in nociceptive and inflammatory processing in rats", Peptides, vol. 32, No. 12, Dec. 1, 2011, pp. 2407-2417.
Naono, R., et al., 'Leucine at the carboxyl-terminal of endokinins C and D contributes to elicitation of the antagonistic effect on substance P in rat pain processing', Brain Res. , 2007, vol. 1165, pp. 71-80.
Medeiros, M. D. S., et al., 'Metabolic stability of some tachykinin analogues to cell-surface peptidases: roles for endopeptidase-24.11 and aminopeptidase N', Peptides, 1995, vol. 16, No. 3, pp. 441-447.
Folkers, K., et al., 'Biological evaluation of substance P antagonists', Br. J. Pharmacol., 1984, vol. 83, pp. 449-456.
Cummings, J., et al., 'Stability and in vitro metabolism of the mitogenic neuropeptide antagonists [D-Arg1, D-Phe5, DTrp7,9, Leu11]-substance P and [Arg6, D-Trp7,9, MePhe8]-substance P (6-11) characterized by high-performance liquid chromatography', J. Pharm. Biomed. Anal., 1994, vol. 12, No. 6, pp. 811-819.

* cited by examiner

*Primary Examiner* — Karlheinz R Skowronek
*Assistant Examiner* — Lianko Garyu
(74) *Attorney, Agent, or Firm* — Lucas & Mercanti, LLP

(57) ABSTRACT

The present invention provides peptides capable of sustaining antagonist activity against substance P for long periods of time. A peptide selected from (a) to (d) can sustain antagonist activity against substance P, analgesic activity, and anti-inflammation activity for a long period of time:

(SEQ ID NO: 3)
(a) Ala-Tyr-Gln-Leu-Glu-His-Thr-DTrp-Gln-Gly-Leu-Leu-NH$_2$;

(b) a peptide consisting of a partial sequence of (a), which consists of 6 to 11 consecutive amino acids comprising at least the C-terminal Thr-DTrp-Gln-Gly-Leu-Leu-NH$_2$ (SEQ ID NO: 18);

(c) Ala-Tyr-Gln-Leu-Glu-His-Thr-Phe-Gln-DTrp-Leu-Leu-NH$_2$ (SEQ ID NO: 4); and (d) a peptide consisting of a partial sequence of (c), which consists of 6 to 11 consecutive amino acids comprising at least the C-terminal Thr-Phe-Gln-DTrp-Leu-Leu-NH$_2$ (SEQ ID NO: 8).

7 Claims, 15 Drawing Sheets

Time (min) after administration of saline or D-EKC/D(3)

ENDOKININ C/D-DERIVED PEPTIDES

CROSS-REFERENCE TO RELATED APPLICATIONS

This application is a 371 of PCT/JP2010/059203, filed on May 31, 2010, which claims the benefit of Japanese Patent Application No. 2009-133339, filed on Jun. 2, 2009, the contents of each of which are incorporated herein by reference.

TECHNICAL FIELD

The present invention relates to a therapeutic agent for pain, a therapeutic agent for inflammation, and a therapeutic agent for itch comprising EKC/D-derived peptides.

BACKGROUND ART

Substance P (hereinafter, referred to as "SP") is a peptide consisting of 11 amino acids, and the amino acid sequence thereof is Arg-Pro-Lys-Pro-Gln-Gln-Phe-Phe-Gly-Leu-Met-NH$_2$ (SEQ ID NO: 10), wherein a carboxyl group of a C-terminal amino acid is amidated, and the same applies below.

SP belongs to the tachykinin peptide family. Here, the term "tachykinin peptide family" (or "tachykinin family") refers to a peptide family having FXGLM-NH$_2$ (SEQ ID NO: 22) where X denotes a hydrophobic amino acid) at the C-terminus. SP is found not only in vertebrates, but also in invertebrates. It is involved in inflammation, pain, itch, muscular contraction, and the like, and it has various functions in an organism. Therefore, the discovery of a novel antagonist against SP is thought to contribute to the development of remedies for suppressing various symptoms in which SP is involved (e.g., pain, inflammation, and itch).

Antagonists against SP have been developed on the basis of non-peptide-derived antagonists and peptide-derived antagonists. Non-peptide-derived antagonists can be synthesized in large amounts, but the antagonists that have been developed to date are problematic in that they dissolve only in organic solvents and can cause adverse reactions when they are administered to an organism. On the other hand, peptide-derived antagonists are advantageous in that they are water soluble. Hence, adverse reactions in an organism caused by peptide-derived antagonists less severe than adverse reactions caused by non-peptide derived antagonists. Therefore, peptide-derived antagonists have a higher utility value than non-peptide-derived antagonists in view of administration to an organism.

Meanwhile, endokinins (hereinafter, referred to as "EK") are novel peptides discovered in 2003. Four types of endokinin are known: endokinin A (hereinafter, referred to as "EKA"), endokinin B (hereinafter, referred to as "EKB"), endokinin C (hereinafter, referred to as "EKC"), and endokinin D (hereinafter, referred to as "EKD") (Non-patent document 1). Among EKs, EKC and EKD are referred to as tachykinin-related peptides, since they both have FXGLL-NH$_2$ (SEQ ID NO: 23; where X denotes hydrophobic amino acid) instead of FXGLM-NH$_2$ (SEQ ID NO: 22) that is a C-terminal consensus sequence of tachykinin peptides. In FXGLL-NH$_2$ (SEQ ID NO: 23), "M" in FXGLM-NH$_2$(SEQ ID NO: 22) is substituted with "L" (Non-patent document 2).

EKC and EKD are peptides each consisting of 14 amino acids. Both EKC and EKD have a consensus amino acid sequence except for the N-terminal 2 amino acids. The present inventors have discovered that intrathecal administration of a peptide (hereinafter, referred to as "EKC/D" and consisting of the amino acid sequence represented by SEQ ID NO: 1) consisting of the consensus amino acid sequence of these peptides to a rat does not induce scratching behavior or thermal hyperalgesia, which is pain-related behavior, whereas pre-administration of the peptide suppresses scratching behavior and thermal hyperalgesia induced by administration of SP or EKA/B (Non-patent document 3). The results indicate that EKC/D acts as an antagonist against SP.

The present inventors have also discovered that scratching behavior and thermal hyperalgesia induced by SP administration are suppressed by intrathecal administration of synthetic peptides in which M in the C-terminus of SP and EKA/B is substituted with L to a rat, as in Patent document 1. Specifically, they have discovered that these synthetic peptides act as antagonists against SP.

Also, Substance P-derived antagonists wherein some amino acids of SP are substituted with D-type amino acids,

```
antagonist D:
                                              (SEQ ID NO: 11)
DArg-Pro-Lys-Pro-DPhe-Gln-DTrp-Phe-DTrp-Leu-Leu-NH2
and Spantide I:
                                              (SEQ ID NO: 12)
DArg-Pro-Lys-Pro-Gln-Gln-DTrp-Phe-DTrp-Leu-Leu-NH2
```

(wherein DArg, DTrp, and DPhe denote D-arginine, D-tryptophan, and D-phenylalanine, respectively. Hereinafter, D-type amino acids are similarly denoted) have been reported (Non-patent document 4 (Antagonist D) and Non-patent document 5 (Spantide I)).

PRIOR ART DOCUMENTS

Patent Documents

Patent document 1 JP Patent Publication (Kokai) No. 2008-156312 A Non-patent documents
Non-patent document 1 Page et al., Proc. Natl. Acad. Sci. U.S.A., 2003, vol. 100, p. 6245-6250
Non-patent document 2 Nigel M. Page, Peptides, 2005, vol. 26, p. 1356-1368
Non-patent document 3 Rumi Naono et al., BRAIN RESEARCH, Jul. 3, 2007, vol. 1165, No. 7, p. 71-80.
Non-patent document 4 Houben, H., Denet, C., 1993. Unexpected effects of peptide and nonpeptide substance P receptor antagonists on basal prolactin and growth hormone release in vitro. Peptides 14, 109-115.
Non-patent document 5 Folkers, K., Hakanson, R., Honig, J., Xu, J. C., Leander, S., 1984. Biological evaluation of substance P antagonists. Br. J. Pharmacol. 83, 449-456.

SUMMARY OF THE INVENTION

Problem to be Solved by the Invention

As described in Non-patent document 3, it is known that EKC/D acts as an antagonist against SP. Although it remains unclear, based on conventional findings, whether or not EKC/D has anti-inflamatory and analgesic effects, the present inventors have revealed that EKC/D has anti-inflamatory and analgesic effects as described in this specifications of Reference examples 1 and 2. However, EKC/D is problematic in that the action of EKC/D as an antagonist against SP disappears within about 1 hour after administration thereof.

Other conventionally known peptide-derived antagonists against SP are not also capable of sustaining the activity at sufficiently satisfactory levels.

Thus, an object of the present invention is to provide peptides capable of sustaining high antagonist activity against SP, high analgesic activity, and anti-inflammatory activity for long periods of time.

Means for Solving the Problem

In order to prolong the antagonist activity of EKC/D against SP, the present inventors substituted some amino acids of EKC/D represented by SEQ ID NO: 1 with D-type amino acids and then confirmed the activity. As a result, unexpectedly, the antagonistic activity against SP of a peptide in which both the $8^{th}$ amino acid, Phe, and the $10^{th}$ amino acid, Gly, in SEQ ID NO: 1 had been substituted with D-tryptophan (DTrp) disappeared within about 1 hour. It was thus confirmed that the ability to sustain the activity of the peptide is the same as that of EKC/D which consists only of L-type amino acids. However, surprisingly, the peptide (SEQ ID NO: 3 or 4) in which either the $8^{th}$ amino acid, Phe, or the $10^{th}$ amino acid, Gly, of EKC/D represented by SEQ ID NO: 1 had been substituted with D-tryptophan (DTrp) showed sustaining its antagonist activity against SP for long periods of time, and the activity itself was significantly improved. The present inventors thus discovered the new facts and completed the present invention.

In order to increase the tissue permeability of a peptide having antagonist activity against SP, the present inventors prepared a plurality of peptide fragments differing in the number of amino acids, in which the N-terminal-side amino acid residues thereof had been deleted, and they then confirmed the antagonist activity of each peptide fragment. As a result, they discovered that a peptide fragment consisting of a partial sequence with a length of 6 residues or more including the C-terminus has significant antagonist activity against SP and good ability to sustain activity.

Furthermore, the analgesic effects and anti-inflammatory effects of the above-mentioned peptides can also be confirmed in the evaluation system without using SP.

The present invention encompasses the following (1) to (19).

(1) A peptide of any one of the following (a) to (e):
(a) a peptide consisting of the amino acid sequence represented by

```
                                           (SEQ ID NO: 3)
Ala-Tyr-Gln-Leu-Glu-His-Thr-DTrp-Gln-Gly-Leu-Leu-
NH2;
```

```
                                           (SEQ ID NO: 4)
Ala-Tyr-Gln-Leu-Glu-His-Thr-Phe-Gln-DTrp-Leu-Leu-
NH2;
```

[DTrp denotes D-tryptophan, and C-terminal Leu-NH$_2$ denotes Leu in which a carboxyl group is amidated];
(b) a peptide consisting of a partial sequence in the amino acid sequence of SEQ ID NO: 3, which consists of 6 to 11 consecutive amino acids comprising at least C-terminal Thr-DTrp-Gln-Gly-Leu-Leu-NH$_2$ (SEQ ID NO: 18);
(c) a peptide consisting of the amino acid sequence represented by Ala-Tyr-Gln-Leu-Glu-His-Thr-Phe-Gln-DTrp-Leu-Leu-NH$_2$ (SEQ ID NO: 4)
[DTrp denotes D-tryptophan and C-terminal Leu-NH$_2$ denotes Leu in which a carboxyl group is amidated];
(d) a peptide consisting of a partial sequence in the amino acid sequence of SEQ ID NO: 4, which consists of 6 to 11 consecutive amino acids comprising at least C-terminal Thr-Phe-Gln-DTrp-Leu-Leu-NH$_2$ (SEQ ID NO: 8); and
(e) a peptide consisting of an amino acid sequence having a deletion, a substitution, or an addition of one or several amino acids at a position other than DTrp and C-terminal Leu-NH$_2$ in the amino acid sequence of any one of peptides (a) to (d) above and having at least one type of activity selected from the group consisting of antagonist activity against substance P, analgesic activity, and anti-inflammatory activity.
(2) An antagonist against substance P, consisting of the peptide according to (1).
(3) A therapeutic agent for pain, comprising the peptide according to (1) as an active ingredient.
(4) A therapeutic agent for inflammation, comprising the peptide according to (1) as an active ingredient.
(5) A therapeutic agent for itch, comprising the peptide according to (1) as an active ingredient.

The present invention further encompasses the following embodiments.
(6) A method for suppressing in vitro or in vivo the functions of substance P, comprising a step of bringing the peptide according to (1) into contact with substance P in vitro or in vivo.
(7) The peptide according to (1) for use in suppression of the functions of substance P in vitro or in vivo.
(8) Use of the peptide according to (1) in production of an antagonist against substance P.
(9) The peptide according to (1) for use as a medicament.
(10) A pharmaceutical composition, comprising the peptide according to (1), and a pharmaceutically acceptable carrier and/or an excipient.
(11) A therapeutic agent for pain, comprising a step of administering the peptide according to (1) in an effective dose to a subject that requires pain treatment.
(12) The peptide according to (1) for use in treatment of pain.
(13) Use of the peptide according to (1) in production of a medicament for treating pain.
(14) A therapeutic agent for inflammation, comprising a step of administering the peptide according to (1) in an effective dose to a subject that requires treatment of inflammation.
(15) The peptide according to (1) for use in treatment of inflammation.
(16) Use of the peptide according to (1) in production of a medicament for treating inflammation.
(17) A therapeutic agent for itch, comprising a step of administering the peptide according to (1) in an effective dose to a subject that requires treatment of itch.
(18) The peptide according to (1) for use in treatment of itch.
(19) Use of the peptide according to (1) in production of a medicament for treating itch.

In the present invention, the term "treatment" used with reference to a symptom refers to, in addition to suppression of a symptom of a subject that has already experienced the symptom, suppression (that is, prevention) of the onset of a symptom of a subject that has not experienced such symptom.

This description includes part or all of the contents as disclosed in the description and/or drawings of Japanese Patent Application No. 2009-133339, which is a priority document of the present application.

Effects of Invention

EKC/D-derived peptides provided by the present invention have high antagonist effects against SP, analgesic effects, and anti-inflammatory effects, and can sustain such effects in vivo over long periods of time.

Also, among EKC/D-derived peptides provided by the present invention, peptides having 6 to 11 amino acids have permeability superior even to that of living tissue while maintaining the above effects.

EMBODIMENTS FOR CARRYING OUT THE INVENTION

Figure 1:
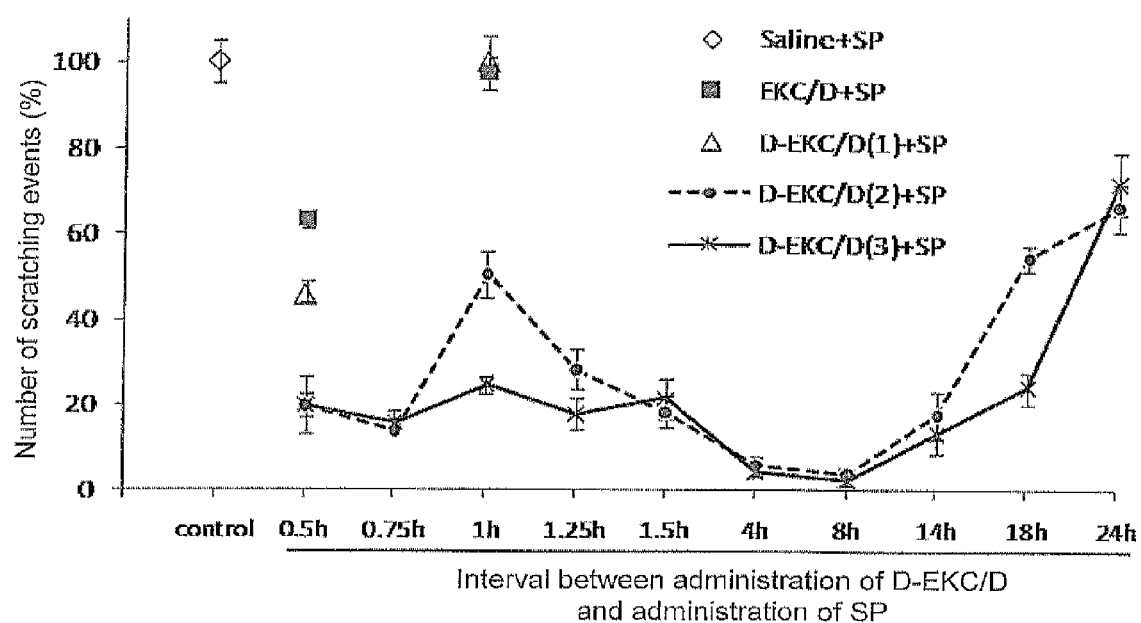
FIG. 1 shows the suppressive effects of peptides synthesized by substituting one of or both the 8th amino acid and the 10th amino acid of EKC/D with D-type amino acid(s) on substance P-induced scratching behavior.

The present invention will be further described in detail.
The peptide according to the present invention consists of the amino acid sequence that is (SEQ ID NO: 3)
Ala-Tyr-Gln-Leu-Glu-His-Thr-DTrp-Gln-Gly-Leu-Leu-NH₂ or (SEQ ID NO: 4)
Ala-Tyr-Gln-Leu-Glu-His-Thr-Phe-Gln-DTrp-Leu-Leu-NH₂

[where DTrp denotes D-tryptophan and C-terminal Leu-NH₂ denotes Leu in which a carboxyl group is amidated, and the same applies below].

Through administration of the peptide(s) according to the present invention to an animal such as a human, pain-related behavior, thermal hyperalgesia, inflammation, itch, and the like resulting from SP can be suppressed. Such suppressive effects can also be confirmed with the evaluation system without using SR. These peptides are not easily degraded in vivo and capable of sustaining antagonist activity against SP, analgesic activity, and anti-inflammatory activity for long periods of time.

In the present invention, it was discovered that a peptide fragment consisting of a partial sequence of 6 or more consecutive amino acids from the C terminus of the EKC/D-derived peptide similarly has good antagonist activity against SP, pain control activity, and anti-inflammation activity. Such a fragment is particularly preferable since it has good permeability to living tissue. Specific examples of preferable peptides include: a peptide consisting of a partial sequence in the amino acid sequence of SEQ ID NO: 3, which consists of 6 to 11 consecutive amino acids and at least comprises the C-terminal Thr-DTrp-Gln-Gly-Leu-Leu-NH₂ (SEQ ID NO: 18); and a peptide consisting of a partial sequence in the amino acid sequence of SEQ ID NO: 4, which consists of 6 to 11 consecutive amino acids and at least comprises the C-terminal Thr-Phe-Gln-DTrp-Leu-Leu-NH₂ (SEQ ID NO: 8). More specific examples of such a fragment include peptides consisting of the following amino acid sequences.

(SEQ ID NO: 13)
Tyr-Gln-Leu-Glu-His-Thr-DTrp-Gln-Gly-Leu-Leu-NH₂

(SEQ ID NO: 14)
Gln-Leu-Glu-His-Thr-DTrp-Gln-Gly-Leu-Leu-NH₂

(SEQ ID NO: 15)
Leu-Glu-His-Thr-DTrp-Gln-Gly-Leu-Leu-NH₂

(SEQ ID NO: 16)
Glu-His-Thr-DTrp-Gln-Gly-Leu-Leu-NH₂

(SEQ ID NO: 17)
His-Thr-DTrp-Gln-Gly-Leu-Leu-NH₂

(SEQ ID NO: 18)
Thr-DTrp-Gln-Gly-Leu-Leu-NH₂

(SEQ ID NO: 19)
Tyr-Gln-Leu-Glu-His-Thr-Phe-Gln-DTrp-Leu-Leu-NH₂

(SEQ ID NO: 20)
Gln-Leu-Glu-His-Thr-Phe-Gln-DTrp-Leu-Leu-NH₂

(SEQ ID NO: 5)
Leu-Glu-His-Thr-Phe-Gln-DTrp-Leu-Leu-NH₂

(SEQ ID NO: 6)
Glu-His-Thr-Phe-Gln-DTrp-Leu-Leu-NH₂

(SEQ ID NO: 7)
His-Thr-Phe-Gln-DTrp-Leu-Leu-NH₂

(SEQ ID NO: 8)
Thr-Phe-Gln-DTrp-Leu-Leu-NH₂

Also, the peptide according to the present invention may be a peptide consisting of an amino acid sequence having a deletion, a substitution, or an addition of 1 or several (e.g., 1 to 5, preferably 1 to 3, and particularly preferably 1 or 2) amino acids with respect to the above amino acid sequence(s) at a position(s) other than DTrp and C-terminal Leu-NH₂, and having at least one activity selected from the group consisting of antagonist activity against SP, analgesic activity, and anti-inflammatory activity.

Here, the term "antagonist activity against SP" refers to activity of suppressing pain-related behavior and thermal hyperalgesia resulting from SP. The activity of suppressing pain-related behavior (resulting from SP) of a peptide can be evaluated according to procedures as described in Examples 1 to 3. The activity of suppressing thermal hyperalgesia (resulting from SP) of a peptide can be evaluated according to procedures described in patent document 1.

A method for evaluating analgesic activity and anti-inflammatory activity of peptides can be performed according to evaluation procedures described in Examples.

The peptide according to the present invention can be chemically synthesized by a known peptide synthesis method. Alternatively, the peptide according to the present invention can be obtained by introducing DNA encoding the peptide according to the present invention into a host and then recovering the thus expressed peptide according to the present invention.

Meanwhile, SP is known to be involved in many symptoms (e.g., pain, inflammation, and itch) (Pharmacological Reviews 54 (2002) 285-322). Accordingly, containment of the peptide according to the present invention as an active ingredient can lead to treatment or suppression of one or more of the following disease states in humans (physiological disorders, symptoms, or diseases): pain related disorders (e.g., hemicrania, neuropathic pain, postoperative pain, chronic pain syndrome); inflammatory diseases (e.g., arthritis and psoriasis); and dermopathy (e.g., atopic dermatitis, contact dermatitis, and herpes zoster).

Examples of the dosage forms of the therapeutic agent for pain, the therapeutic agent for inflammation, or the therapeutic agent for itch according to the present invention include, but are not particularly limited to, oral preparations such as tablets, dust formulations, emulsions, capsules, granules, subtle granules, powders, solutions, syrups, suspensions, and elixirs, or parenteral preparations such as injection preparations, drops, suppositories, inhalers, transdermal absorbents, transmucosal absorbents, adhesive preparations, sprays, and ointments.

Examples of pharmaceutical ingredients that can be combined with the peptide according to the present invention include excipients, binders, disintegrators, surfactants, lubricants, fluid accelerators, flavoring agents, colorants, and aroma chemicals.

Examples of excipients include starch, lactose, saccharose, mannite, carboxymethylcellulose, corn starch, and inorganic salts.

Examples of binders include crystalline cellulose, crystalline sodium cellulose.carmellose, methylcellulose, hydroxypropyl cellulose, low substituted hydroxypropyl cellulose, hydroxypropyl methylcellulose, hydroxypropyl methylcellulose phthalate, hydroxypropyl methylcellulose acetate succinate, sodium carmellose, ethyl cellulose, carboxy methyl ethyl cellulose, hydroxyethyl cellulose, wheat starch, rice starch, corn starch, potato starch, dextrin, gelatinized starch, partially gelatinized starch, hydroxypropyl starch, pullulan, polyvinylpyrrolidone, aminoalkyl methacrylate copolymer E, aminoalkyl methacrylate copolymer RS, methacrylate copolymer L, methacrylate copolymer, polyvinyl acetal diethyl aminoacetate, polyvinyl alcohol, gum Arabic, powdered acacia, agar, gelatin, white shellac, tragacanth, purified saccharose, and macrogol.

Examples of disintegrators include crystalline cellulose, methylcellulose, low substituted hydroxypropyl cellulose, carmellose, carmellose calcium, sodium carmellose, croscarmellose sodium, wheat starch, rice starch, corn starch, potato starch, partial gelatinized starch, hydroxypropyl starch, sodium carboxymethyl starch, and tragacanth.

Examples of surfactants include soybean lecithin, sucrose fatty acid ester, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, and lauromacrogol.

Examples of lubricants include wheat starch, rice starch, corn starch, stearic acid, calcium stearate, magnesium stearate, hydrous silicon dioxide, light anhydrous silicic acid, synthetic aluminum silicate, dried aluminum hydroxide gel, talc, magnesium aluminometasilicate, calcium hydrogen phosphate, anhydrous calcium hydrogen phosphate, sucrose fatty acid ester, waxes, hydrogenated plant oil, and polyethylene glycol.

Examples of fluid accelerators include hydrous silicon dioxide, light anhydrous silicic acid, dried aluminum hydroxide gel, synthetic aluminum silicate, and magnesium silicate.

Also, when the dosage form of the therapeutic agent for pain or the therapeutic agent for inflammation according to the present invention is a solution, a syrup, a suspension, an emulsion, or an elixir, it may contain a taste and flavor corrigent, a colorant, and the like.

Moreover, the therapeutic agent for pain or the therapeutic agent for inflammation according to the present invention may further contain other ingredients. Examples of ingredients that can be contained in the therapeutic agent for pain or the therapeutic agent for inflammation according to the present invention include, propionic acid derivative-based nonsteroidal antiinflammatory drugs such as propionic acid derivatives (e.g., ibuprofen, ketoprofen, flurbirofen, flurbirofen axetil, oxaprozin, fenoprofen, tiaprofenic acid, naproxen, pranoprofen, loxoprofen, aminoprofen, zartoprofen, or salts thereof), non-pyrine-based antipyretic analgesics such as acetaminophen, dimetotiazine mesilate, or salts thereof, antiplasmin agents such as tranexamic acid, epsilon aminocaproic acid, or salts thereof, and anti-inflammatory enzyme drugs such as lysozyme chloride, semialkaline proteinase, serrapeptase, bromelain, or salts thereof.

Meanwhile, the content of the peptide according to the present invention in the therapeutic agent for pain, the therapeutic agent for inflammation, or the therapeutic agent for itch according to the present invention can be appropriately varied depending on purposes of administration, routes of administration, dosage forms, and the like. For example, the content ranges from 0.001 mg to 1 mg and preferably ranges from 0.001 mg to 0.01 mg.

The frequency of administration, dosage, and duration of administration for the therapeutic agent for pain, the therapeutic agent for inflammation, or the therapeutic agent for itch according to the present invention are not particularly limited and can be appropriately determined depending on disease type, patient age, gender, body weight, or the degree of severity of symptoms, route of administration, and the like. The frequency of administration ranges from once to three times a day and is preferably once a day in the case of external use. The dosages of the peptide according to the present invention contained in the therapeutic agent for pain, the therapeutic agent for inflammation, or the therapeutic agent for itch according to the present invention are as described below. Based on the dosage of indomethacin, which is 50 mg for external use and is 1 mg for intravenous injection, it is estimated that the dosage of the peptide for intravenous injection ranges from 0.01 mg to 1 mg per kg of body weight per day and preferably ranges from 0.01 mg to 0.1 mg per kg of body weight, and that the dosage of the peptide for external use is 50 times greater than the dosage for intravenous injection. Also, the duration of administration ranges from 1 to 7 days and preferably ranges from 1 to 2 days, for example.

The routes of administration of the therapeutic agent for pain, the therapeutic agent for inflammation, or the therapeutic agent for itch according to the present invention can be appropriately determined depending on dosage forms or purposes for use. Examples of the routes of administration include peroral administration, parenteral administration (e.g., intrathecal administration, intraperitoneal administration, intravenous administration, intramuscular administration, subcutaneous administration, intrarectal administration, intranasal administration, and sublingual administration) and local administration (transdermal patches, lotions, solutions, aerosol agents, gel, cream pharmaceuticals, ointments, adhesive skin patches).

Pharmacological assessment for the therapeutic agent for pain or the therapeutic agent for inflammation according to the present invention can be performed as follows, for example.

Pharmacological assessment for the therapeutic agent for pain can be performed using rats. Specifically, SP is intrathecally administered to rats, so as to cause pain-related behavior resulting from SP (e.g., thermal hyperalgesia and scratching behavior). First, the therapeutic agent for pain according to the present invention is intrathecally administered to a rat, SP is then intrathecally administered to the rat, and then the rat is compared with a rat (negative control not treated with the therapeutic agent for pain according to the present invention) to which only SP has been administered. If scratching behavior or thermal hyperalgesia is significantly reduced, it can be determined that the therapeutic agent for pain according to the present invention is effective.

Also, pharmacological assessment for the therapeutic agent for inflammation can be performed using rats. Specifically, an inflammation-inducing agent (e.g., carrageenan) is subcutaneously injected to rat plantar to induce inflammation, so as to cause increases in paw size and hyperalgesia, for example. Subsequently, the therapeutic agent for inflammation according to the present invention is intrathecally administered or administered to an inflammatory site, and then the rat is compared with a rat (negative control) to which the therapeutic agent for inflammation according to the present invention has not been administered. If paw size or hyperalgesia is found to have significantly decreased, it can be determined that the therapeutic agent for inflammation according to the present invention is effective against inflammation.

With the peptide according to the present invention as described above, scratching behavior and thermal hyperalgesia resulting from SP can be significantly suppressed. Furthermore, the therapeutic agent for pain, the therapeutic agent for inflammation, or the therapeutic agent for itch according to the present invention comprises the peptide according to the present invention as an active ingredient. An effective dose thereof is administered to an animal such as a human regardless of age and gender, so that pain and inflammation can be suppressed in vivo.

EXAMPLES

The present invention will be more specifically described below by referring to Examples, but the technical scope of the present invention is not limited to these Examples.

In addition, the term "administration" in the following Examples 1 to 4 refers to intrathecal administration to rats.

Example 1

Improvement of Activity Via Substitution of Some Amino Acids in EKC/D with D-Type Amino Acids Background Endokinin C (hereinafter, referred to as "EKC") and endokinin D (hereinafter, referred to as "EKD") are peptides each consisting of 14 amino acids and share a consensus amino acid sequence other than the two N-terminal amino acids. The present inventors discovered that administration of a peptide (hereinafter, referred to as "EKC/D"; amino acid sequence: SEQ ID NO: 1) consisting of the consensus amino acid sequence (the number of amino acids: 12) of the two peptides to a rat suppresses substance P-induced scratching behavior and thermal hyperalgesia. Moreover, EKC/D has anti-inflammatory and analgesic effects as demonstrated in the following Reference examples 1 and 2.

In general, it is known that substitution of some amino acids with D-type amino acids in peptides consisting of L-type amino acids delays the in vivo degradation of the peptides and prolongs the duration of effectiveness. However, the positions of amino acids in EKC and EKD to be substituted with D-type amino acids so as to cause effective results have not yet been reported. Hence, in Example 1, peptides were synthesized by substituting some amino acids of EKC/D with D-type amino acids with reference to a substance P-derived antagonist, and then the effects of improving the activity were confirmed. Substance P is a peptide consisting of the amino acid sequence of SEQ ID NO: 10 (consisting of 11 amino acids).

Antagonists reported to date that are prepared by substituting some amino acids of substance P with D-type amino acids are Antagonist D (SEQ ID NO: 11) and Spantide I (SEQ ID NO: 12), as listed in the Background Art. Common features shared by these antagonists are that the $7^{th}$ Phe and the $9^{th}$ Gly of substance P are each substituted with D-Trp, and Met located at the C-terminus is substituted with Leu. The N-terminal amino acid of EKC/D is Leu. Hence, it is suggested that EKC/D can have antagonistic effects against the substance P receptor.

The consensus amino acid sequence of tachykinin peptides including substance P is Phe-X-Gly-Leu-Met-$NH_2$ (SEQ ID NO: 22). In Example 1, peptides were synthesized from EKC/D:

(SEQ ID NO: 1)
Ala-Tyr-Gln-Leu-Glu-His-Thr-Phe-Gln-Gly-Leu-Leu-$NH_2$.

Specifically, a peptide [D-Trp$^{8,10}$]-EKC/D (hereinafter, also referred to as "D-EKC/D(1)"):

(SEQ ID NO: 2)
Ala-Tyr-Gln-Leu-Glu-His-Thr-DTrp-Gln-DTrp-Leu-Leu-$NH_2$ was synthesized by substituting the $8^{th}$ Phe and the $10^{th}$ Gly with DTrp, a peptide [D-Trp$^8$]-EKC/D (hereinafter, also referred to as "D-EKC/D(2)"):

(SEQ ID NO: 3)
Ala-Tyr-Gln-Leu-Glu-His-Thr-DTrp-Gln-Gly-Leu-Leu-NH$_2$ was synthesized by substituting the 8$^{th}$ Phe with D-Trp, and a peptide [D-Trp$^{10}$]-EKC/D (hereinafter, also referred to as "D-EKC/D(3)"):

(SEQ ID NO: 4)
Ala-Tyr-Gln-Leu-Glu-His-Thr-Phe-Gln-DTrp-Leu-Leu-NH$_2$ was synthesized by substituting the 10$^{th}$ Gly with D-Trp. Then the effects of each synthetic peptide against substance P-induced scratching behavior were evaluated.

Experiments and Results

In Example 1, 10$^{-3}$M (10 nmol/10 μl) EKC/D or D-EKC/D (1), (2) or (3) was administered to intrathecally catheterized rats via catheters. After the predetermined time periods denoted on the horizontal axis in FIG. 1, the numbers of scratching events (scratching behavior) induced by intrathecal administration of 10$^{-3}$M (10 nmol/10 μl) substance P (hereafter, referred to as "SP") were determined. Here, the expression "10$^{-3}$M (10 nmol/10 μl) EKC/D or D-EKC/D (1), (2), or (3) was administered" refers to a situation in which 10 μl in total of a solution (that is, 10$^{-3}$M solution) containing 10 nmol of EKC/D or D-EKC/D (1), (2), or (3) was all administered. The expression, " . . . administration of 10$^{-3}$M substance P (10 nmol/10 μl)" refers to a situation in which 10 μl in total of a solution (that is, 10$^{-3}$M solution) containing 10 nmol of the substance was all administered. The same similarly applies below.

Meanwhile, saline (10 μl) was intrathecally administered to intrathecally catheterized rats via catheters and then, after 30 minutes, 10$^{-3}$M SP (10 nmol/10 μl) was intrathecally administered to the rats. The number of the thus induced scratching events was determined to be the number of scratching events in the control group. The control group is denoted with saline-4-SP in FIG. 1.

The vertical axis of the graph in FIG. 1 indicates changes in the numbers of scratching events (represented by relative values) due to administration of 10$^{-3}$M EKC/D or D-EKC/D (1), (2), or (3) when the number of scratching events (of untreated rats in a control group) induced by intrathecal administration of 10$^{-3}$M substance P was determined to be 100%. Meanwhile, the horizontal axis indicates the intervals between the administration of EKC/D, D-EKC/D (1), (2), or (3) and 10$^{-3}$M substance P.

10$^{-3}$M substance P was administered at 30 minutes after intrathecal administration of 10$^{-3}$M EKC/D consisting of L-type amino acids alone. The number of scratching events induced by substance P decreased to about 60%. However, the number of scratching events induced by administration of substance P had been restored 1 hour later to the same degree as that for the control group (saline+SP) (EKC/D+SP). These results indicate that EKC/D suppresses substance P-induced scratching behavior, but the effects disappear within 1 hour. Next, 10$^{-3}$ M substance P was administered at 30 minutes after administration of 10$^{-3}$M [D-Trp$^{8,10}$]-EKC/D. The number of scratching events induced by substance P decreased to about 40%. However, when substance P was administered at 1 hour after administration of 10$^{-3}$M [D-Trp$^{8,10}$]-EKC/D, suppressive effects due to [D-Trp$^{8,10}$]-EKC/D disappeared (D-EKC/D(1)+SP). These results indicate that substitution of both the 8$^{th}$ and the 10$^{th}$ amino acids with DTrp slightly enhances the effects of [D-Trp$^{8,10}$]-EKC/D within 30 minutes, but the duration of effectiveness of the peptide is almost the same as that of the EKC/D consisting only of L-type amino acids. Therefore, such method of substituting the 8$^{th}$ and the 10$^{th}$ amino acids with DTrp is not considered effective. However, interesting results were obtained from experiments in which [D-Trp$^{8}$]-EKC/D or [D-Trp$^{10}$]-EKC/D was administered. When 10$^{-3}$M substance P was administered at 30 minutes after administration of the two peptides (10$^{-3}$M), the number of scratching events resulting from administration of substance P decreased to about 20% compared with the case of the control group (saline+SP). In the case of an administration interval of 45 minutes, almost the same effects were exhibited. At 1 hour after administration of 10$^{-3}$M [D-Trp$^{8}$]-EKC/D, the number of scratching events induced by 10$^{-3}$M substance P showed a slight tendency of restoration (D-EKC/D(2)+SP), and both peptides sustained their suppressive effects for a maximum of 24 hours (D-EKC/D(2)+SP, D-EKC/D(3)+SP).

Discussion

This Example shows that the substitution of one of the amino acids composing EKC/D with D-type amino acid results in significantly enhanced suppressive effects of EKC/D. According to findings obtained to date, substance P-derived antagonists are mainly prepared by substituting amino acids at two positions with D-type amino acids. However, the effects of [D-Trp$^{8,10}$]-EKC/D in which two of the amino acids composing EKC/D had been substituted with D-type amino acids, as in the case of substance P-derived antagonists, were almost the same as those of EKC/D consisting of L-type amino acids. Thus, it was considered that substitution of amino acids at 2 positions with D-type amino acids results in disappearance of suppressive effects within a short time period. On the other hand, it was revealed that [D-Trp$^{8}$]-EKC/D or [D-Trp$^{10}$]-EKC/D in which one of the amino acids composing EKC/D had been substituted with D-type amino acid exhibited stronger effects of suppressing substance P-induced scratching behavior and the sustained effect was significantly longer than that of EKC/D consisting of L-type amino acids.

Comparative Example 1

With procedures similar to those of Example 1, 10$^{-3}$M (10 nmol/10 μl) Spantide I (SEQ ID NO: 12) was intrathecally administered to catheterized rats via catheters. After the predetermined times indicated by the horizontal axis of FIG. 6, 10$^{-3}$M substance P (10 nmol/10 μl) (hereinafter, referred to as "SP") was intrathecally administered, and then the numbers of scratching induced by SP administration were determined. The results are shown in FIG. 6.

Meanwhile, the number of scratching induced by intrathecal administration of saline (10 μl) to catheterized rats via catheters followed by intrathecal administration of 10$^{-3}$M SP (10 nmol/10 μl) 30 minutes later, was designated as the number of scratching in the control group. The control group is denoted as saline+SP in FIG. 6.

Figure 6:
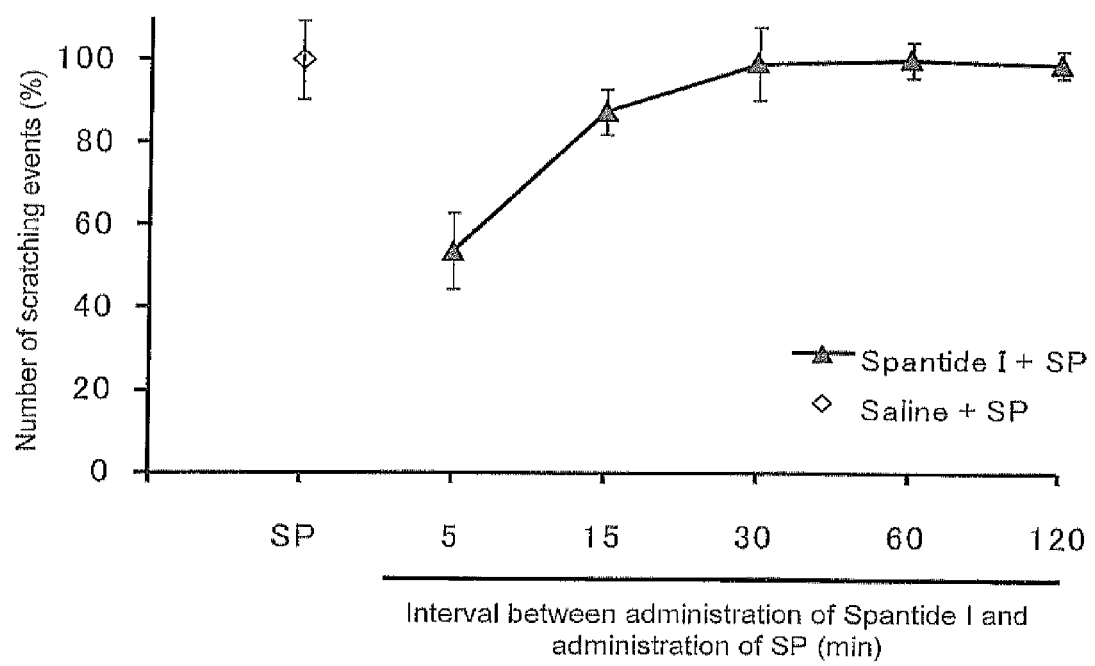
FIG. 6 shows the suppressive effects of Spantide I on substance P-induced scratching behavior.

As shown in FIG. 6, Spantide I suppressed substance P-induced scratching behavior, but the effects disappeared within 30 minutes.

Example 2

Activity of Peptides with Amino Acids Deleted from N-Terminus (1)

Background

As demonstrated by the experimental results in Example 1, 10$^{-3}$M [D-Trp$^{10}$]-EKC/D (10 nmol/10 μl) significantly suppressed scratching behavior induced by intrathecal administration of $10^{-3}$M substance P (10 nmol/10 μl). Meanwhile, the fewer the number of amino acids composing a peptide, the higher the degree of tissue permeation and the higher economic benefits. Such features are more effective for use of the peptide in drug discovery. Hence, peptides were synthesized by deleting the predetermined numbers of amino acids from the N-terminus of [D-Trp$^{10}$]-EKC/D, which is a peptide consisting of 12 amino acids. The scratching behavior-suppressing effects of these peptides were evaluated. In the experiment in Example 1, significant suppressive effects were exhibited with the use of intervals of 4 hours, 8 hours, and 14 hours between the administration of $10^{-3}$M [D-Trp$^{10}$]-EKC/D and the administration of $10^{-3}$M substance P. Accordingly, the intervals between the administration of each test peptide and the administration of substance P were determined to be 4 hours, 8 hours, and 14 hours. The suppressive effects of each test peptide on substance P-induced scratching behavior were examined.

The amino acid sequences of the test peptides used in this experiment are as follows.

```
[D-Trp10]-EKC/D (herinafter, also referred to as
"D-EKC/D (3)"):
                                        (SEQ ID NO: 4)
Ala-Tyr-Gln-Leu-Glu-His-Thr-Phe-Gln-DTrp-Leu-Leu-

NH2

D-EKC/D (4):
                                        (SEQ ID NO: 5)
Leu-Glu-His-Thr-Phe-Gln-DTrp-Leu-Leu-NH2

D-EKC/D (5):
                                        (SEQ ID NO: 6)
Glu-His-Thr-Phe-Gln-DTrp-Leu-Leu-NH2

D-EKC/D (6):
                                        (SEQ ID NO: 7)
His-Thr-Phe-Gln-DTrp-Leu-Leu-NH2
```

Experiment and Results

The test was conducted with procedures similar to those in Example 1 except for 4 hours, 8 hours, and 14 hours of the intervals between the administration of each test peptide and the administration of substance P. The concentration of each test peptide and that of substance P for administration were both determined to be $10^{-3}$M (10 nmol/10 μl), similarly to Example 1. The number of scratching in a control group was determined by procedures similar to those in Example 1, such that substance P was administered at 30 minutes after administration of saline (10 μl) and then the number was determined.

Figure 2:
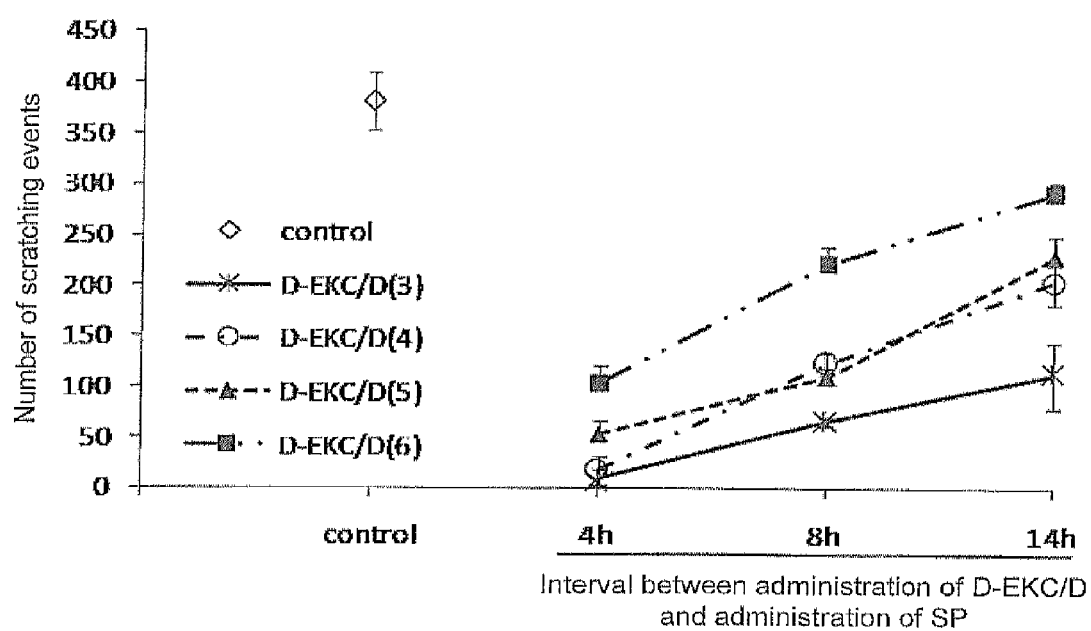
FIG. 2 shows the suppressive effects of D-EKC/D (3) peptide synthesized by substituting the 10th amino acid of EKC/D with D-type amino acid and peptides (D-EKC/D (4)-(6)) prepared by deleting several amino acids from N-terminus of peptide on substance P-induced scratching behavior.

The results are shown in FIG. 2. The vertical axis of the graph in FIG. 2 indicates the numbers of scratching induced by intrathecal administration of $10^{-3}$M substance P and the horizontal axis indicates the intervals between the administration of test peptides and the administration of substance P. The number of scratching induced by $10^{-3}$M substance P was about 380 (control) in the case of the control rat group. When substance P was administered at 4 hours after administration of [D-Trp$^{10}$]-EKC/D, scratching behavior due to substance P was almost never induced, but the suppressive effects of the D-EKC/D (3) peptide were gradually attenuated as the administration interval was prolonged to 8 hours and then to 14 hours. When substance P was administered at 4 hours after administration of [D-Trp$^{10}$]-EKC/D-derived peptide D-EKC/D (4) synthesized by deleting three amino acids (Ala-Tyr-Gln) from the N-terminus of [D-Trp$^{10}$]-EKC/D, similarly to the case of D-EKC/D (3) consisting of 12 amino acids, scratching behavior due to substance P was also never induced and the suppressive effects were gradually attenuated as the administration interval was prolonged to 8 hours and then to 14 hours (D-EKC/D (4)). When substance P was administered at 4 hours after administration of the D-EKC/D (5) peptide synthesized by deleting four amino acids (Ala-Tyr-Gln-Leu) from N-terminus of [D-Trp$^{10}$]-EKC/D, scratching behavior due to substance P was almost never induced, but similarly to the case of D-EKC/D (3) the suppressive effects were gradually attenuated as the administration interval was prolonged (D-EKC/D (5)). Even in the case of the D-EKC/D (6) peptide synthesized by deleting five amino acids (Ala-Tyr-Gln-Leu-Glu) from the N-terminus of this peptide, significant suppressive effects were observed with a 4-hour administration interval, and the suppressive effects of the D-EKC/D(6) peptide were attenuated as the administration interval became shorter to 8 hours and 14 hours (D-EKC/D(6)).

Discussion

Peptides were synthesized by deleting predetermined numbers of consecutive amino acids from the N-terminus of [D-Trp$^{10}$]-EKC/D, and then the effects of these peptides on substance P-induced scratching behavior were evaluated. The D-EKC/D (4) peptide synthesized by deleting three amino acids from the N-terminus of [D-Trp$^{10}$]-EKC/C exhibited suppressive effects almost similar to those of [D-Trp$^{10}$]-EKC/D consisting of 12 amino acids. Thus, it is inferred that a peptide synthesized by deleting 1 to 2 amino acids from the N-terminus exhibits suppressive effects similar to those of [D-Trp$^{10}$]-EKC/D consisting of 12 amino acids.

On the other hand, even in the case of the D-EKC/D (6) peptide consisting of 7 amino acids from the C-terminus, which had been synthesized by deleting five amino acids (Ala-Tyr-Gln-Leu-Glu) from the N-terminus of [D-Trp$^{10}$]-EKC/C, significant suppressive effects were observed with a 4 hour administration interval. Also, it is known that Leu at the C-terminus of EKC/C is important for exhibition of suppressive effects (paragraph [0009], JP Patent Publication (Kokai) No. 2008-156312 A). The phenomenon of the suppressive effects being attenuated as the administration interval is prolonged is considered to suggest that amino acids are degraded from the N-terminus of the peptide and thus attenuate suppressive effects. If this hypothesis is correct, it is indicated that a further decrease in the number of amino acids would result in a [D-Trp$^{10}$]-EKC/D-derived peptide having no suppressive effects.

Example 3

Activity of Peptides with Amino Acids Deleted from the N-Terminus (2)

Background

In Example 2, it was confirmed that even the EKC/D-derived D-EKC/D (6) peptide consisting of 7 amino acids from the C-terminus suppressed scratching behavior due to administration of substance P. This suggests that a peptide consisting of even fewer amino acids can have suppressive effects. Hence, furthermore, peptides each consisting of six or five amino acids from the C-terminus were synthesized and the effects were examined.

In this experiment, in addition to the peptides used in Example 3, peptides consisting of the following amino acid sequences were used as test peptides.

D-EKC/D (7):
Thr-Phe-Gln-DTrp-Leu-Leu-NH$_2$    (SEQ ID NO: 8)

D-EKC/D (8):
Phe-Gln-DTrp-Leu-Leu-NH$_2$    (SEQ ID NO: 9)

Results

The test was conducted with procedures similar to those in Example 1, except for 4 hours of interval between the administration of each test peptide and the administration of substance P. The concentration of each test peptide and that of substance P for administration were determined to be $10^{-3}$M (10 nmol/10 μl), similarly to Example 1. The number of scratching events in the control group was determined with procedures similar to those in Example 1, such that substance P was administered at 30 minutes after administration of saline (10 μl) and then the number was determined.

Figure 3:
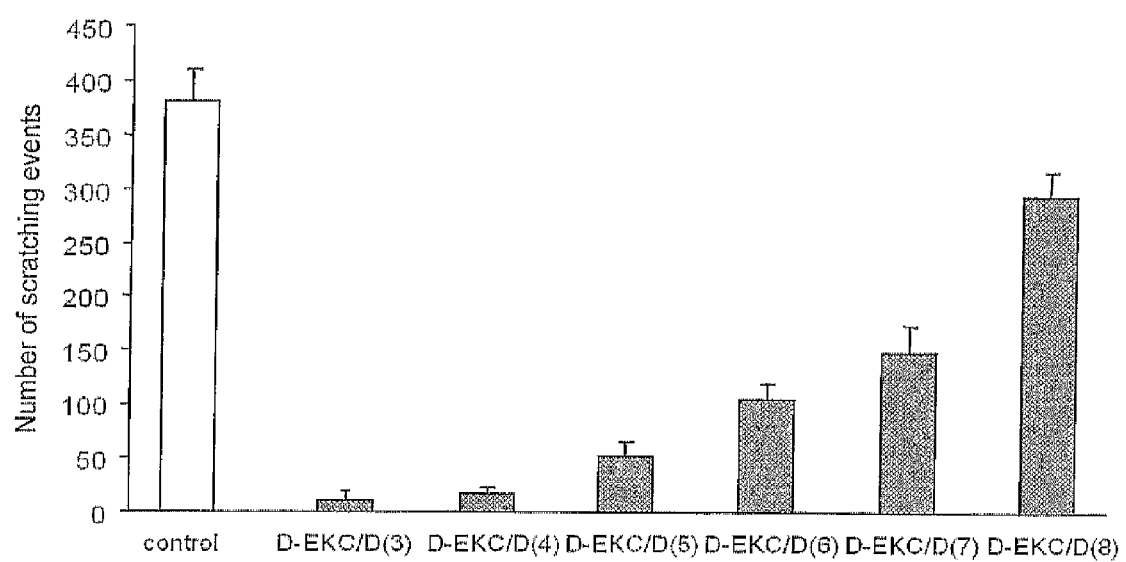
FIG. 3 shows the suppressive effects of D-EKC/D (3) peptide synthesized by substituting the 10th amino acid of EKC/D with D-type amino acid, and peptides (D-EKC/D(4)-(8)) synthesized by deleting several amino acids from N-terminus of peptide on substance P-induced scratching behavior.

The results are shown in FIG. 3. In FIG. 3, the vertical axis of the graph indicates the numbers of scratching induced by administration of $10^{-3}$M substance P, and the horizontal axis indicates [D-Trp$^{10}$]-EKC/D-derived peptides differing in the number of amino acids. The interval between the administration of each test peptide and the administration of substance P was 4 hours. When $10^{-3}$M substance P was administered after administration of saline, the number of scratching was 380 (control). In contrast, when substance P was administered at 4 hours after administration of D-EKC/D (3), scratching behavior was almost never induced (D-EKC/D (3)). The graph in FIG. 3 shows that as the numbers of amino acids decreased in order of D-EKC/D (4), D-EKC/D (5), D-EKC/D (5), D-EKC/D (6), and D-EKC/D (7), the suppressive effects on substance P-induced scratching behavior were attenuated. Almost no suppressive effects were observed for D-EKC/D (8) consisting of five amino acids (D-EKC/D (8)).

Discussion

When substance P was administered at 4 hours after administration of D-EKC/D (8) that was [D-Trp$^{10}$]-EKC/D-derived peptide consisting of five amino acids, the number of scratching was almost the same as that of the control group (without treatment). This suggests that the D-EKC/D (8) peptide had no suppressive effects. Therefore, it can be said that D-EKC/D (7) consisting of six amino acids is an amino acid sequence exhibiting minimum suppressive effects. Also, the graph in FIG. 3 shows that the larger the number of amino acids, the stronger the suppressive effects on the number of scratching.

Reference Example 1

Anti-Inflammatory Effects of EKC/D Consisting of L-Type Amino Acids Alone

Intraplantar injection of carrageenan (which is an inflammation inducing agent) to rats resulted in increased paw size following inflammation. The vertical axis of the graph in FIG. 4 indicates increases (%) in paw size and the horizontal axis indicates the time after administration of saline (100 μl: saline) or EKC/D with "minutes," thereby showing the time course changes of anti-inflammatory effects of EKC/D administration on carrageenan-induced inflammation. The paw size before carrageenan administration was determined to be 100%. Paw size was increased by about 50% (saline) as measured using a paw size meter at 1 hour after carrageenan injection. This state continued for about 60 minutes (saline). Next, at 1 hour after carrageenan injection that resulted in a significant increase in paw size following inflammation, endokinin C/D (EKC/D) (at various concentrations) consisting of L-type amino acids alone were injected, and the effects thereof were evaluated by observing changes in paw size. When $10^{-3}$M EKC/D (100 nmol/100 μl) was injected, paw size had decreased to about 40% at 10 minutes after, to about 20% at 30 minutes after, and to about 40% at 50 minutes after injection. Increases in paw size accompanying inflammation due to carrageenan injection were significantly suppressed (EKC/D $10^{-3}$ M). When $10^{-4}$M EKC/D (10 nmol/100 μl) was injected, paw size had decreased to 40% at 30 minutes after injection and paw size was almost at a normal level at 60 minutes after injection. EKC/D exhibited weak anti-inflammatory effects (EKC/D $10^{-4}$ M). No clear effects could be recognized when $10^{-5}$M EKC/D (1 nmol/100 μl) and $10^{-6}$M EKC/D (100 pmol/100 μl) were injected (EKC/D $10^{-5}$ M and EKC/D $10^{-6}$ M). These results demonstrate that increases in paw size accompanying carrageenan-induced inflammation can be suppressed by injection of EKC/D and that EKC/D has anti-inflammatory effects.

Reference Example 2

Figure 5:
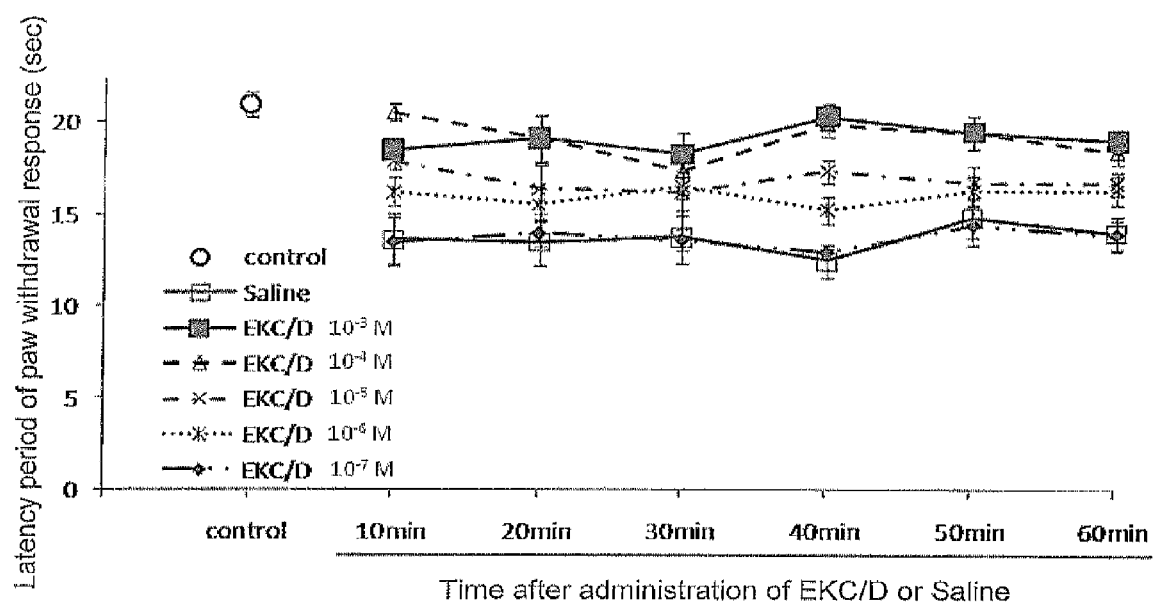
FIG. 5 shows the suppressive effects of EKC/D consisting of L-type amino acids alone on SP-induced thermal hyperalgesia.

Thermal Hyperalgesia-Suppressing Effects of EKC/D Consisting of L-Type Amino Acids Alone Intraplantar injection of carrageenan induces thermal hyperalgesia accompanying inflammation. To examine induction of thermal hyperalgesia, noxious thermal stimulation was applied to plantar using infrared rays. It can be said that thermal hyperalgesia takes place when the latency period of the withdrawal response becomes shorter than that for untreated rats. In FIG. 5, the vertical axis of the graph indicates the latency period in seconds and the horizontal axis of the graph indicates the time after injection of saline or EKC/D in minutes. The latency period in untreated rats (control) after noxious thermal stimulation was about 21 seconds. When saline (100 μl) was injected at 1 hour after carrageenan injection, the latency period was about 13 seconds. This clearly demonstrates that thermal hyperalgesia is induced by carrageenan injection. This state was sustained for 60 minutes (saline). When $10^{-3}$M EKC/D (100 nmol/100 μl) was injected at 1 hour after carrageenan injection, the latency period following noxious thermal stimulation was almost the same as that in the case of untreated rats. It was demonstrated that thermal hyperalgesia accompanying inflammation was suppressed by treatment with EKC/D (EKC/D $10^{-3}$ M). When $10^{-4}$M EKC/D (10 nmol/100 μl) was injected, the effects exhibited herein showed almost the same tendency as that in the case of $10^{-3}$M EKC/D (EKC/D $10^{-4}$ M). When $10^{-5}$M (1 nmol/100 μl) and $10^{-6}$M (100 μmol/100 μl) EKC/D were injected, the latency period before rats responded to noxious thermal stimulation was about 17 seconds, which was longer than that in the case of treatment with saline (EKC/D $10^{-5}$ M and EKC/D $10^{-6}$ M). The latency period following noxious thermal stimulation in the case of injection of $10^{-7}$M EKC/D (10 pmol/100 μl) was almost the same as that in the case of saline (EKC/D $10^{-7}$ M). These results demonstrate that thermal hyperalgesia accompanying inflammation induced by carrageenan can be suppressed by injection of EKC/D at inflammatory sites.

Figure 4:
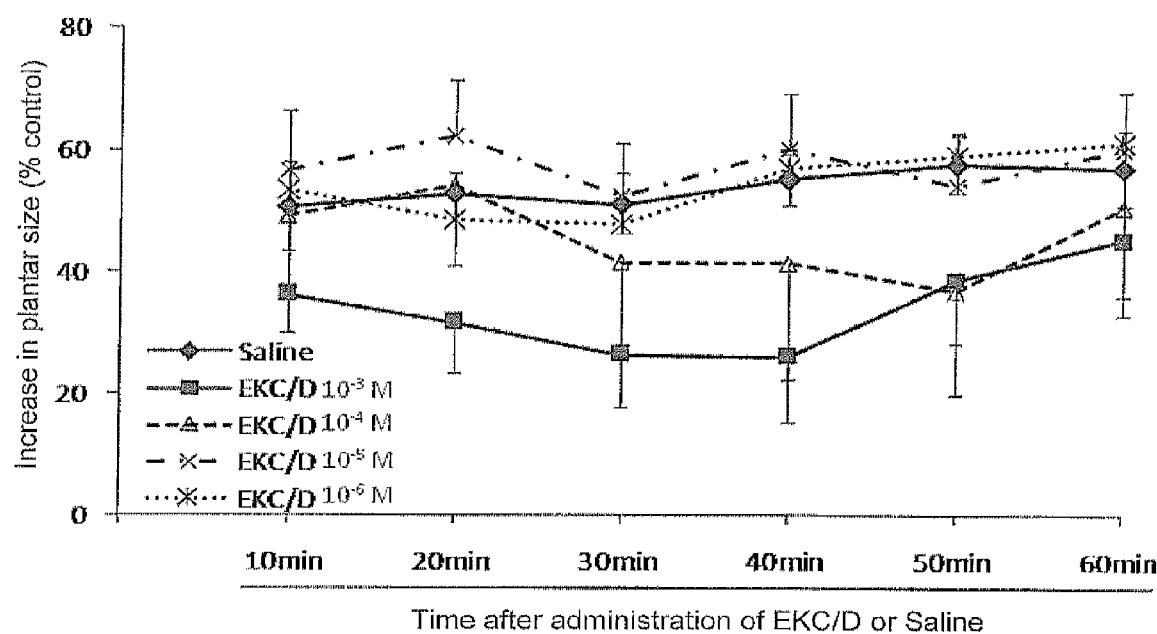
FIG. 4 shows anti-inflammatory effects of EKC/D consisting of L-type amino acids alone.

Taken together with FIG. 4 and FIG. 5, these results indicate that EKC/D suppresses increases in paw size accompanying inflammation and induction of thermal hyperalgesia. Specifically, the results indicate that EKC/D has antiphlogistic and analgetic effects.

Example 4

Effects of Substitution of Some Amino Acids of EKC/D with D-Type Amino Acids on Thermal Hyperalgesia Non-patent document 3 discloses that SP-induced hyperalgesia had been suppressed at 5 minutes after administration of EKC/D in a test for evaluating the effects of preadministration of EKC/D consisting of L-type amino acids alone on hyperalgesia accompanying intrathecal administration of SP.

In this test, the effects of intrathecal pre-administration with D-EKC/D (1), (2), and (3) on the induction of thermal hyperalgesia following intrathecal administration of SP were confirmed using as an index thermal hyperalgesia, which is one type of pain-related behavior. The effects can be evaluated based on withdrawal latency period, which is the time required for withdrawal response to take place after application of noxious thermal stimulation to plantar using infrared rays.

The test was conducted at 4 hours and 8 hours after administration of D-EKC/D (1), (2), or (3) and revealed to exhibit significant suppressive effects on SP-induced thermal hyperalgesia on the basis of experimental results in Example 1.

In Example 4, $10^{-3}$M (10 nmol/10 µl) D-EKC/D (1), (2), or (3) was administered to intrathecally catheterized rats via catheters, intrathecal administration of $10^{-6}$M (10 pmol/10 µl) SP was performed at 4 hours and at 8 hours after administration of D-EKC/D, the presence or the absence of hyperalgesia following intrathecal administration of SP was evaluated based on the time (latency period) required for withdrawal response to take place, the latency period following SP administration in rats pretreated with D-EKC/D and the latency period resulting from administration of SP alone were compared, and thus the effects of preadministration of D-EKC/D (1), (2), and (3) were evaluated.

Figure 7:
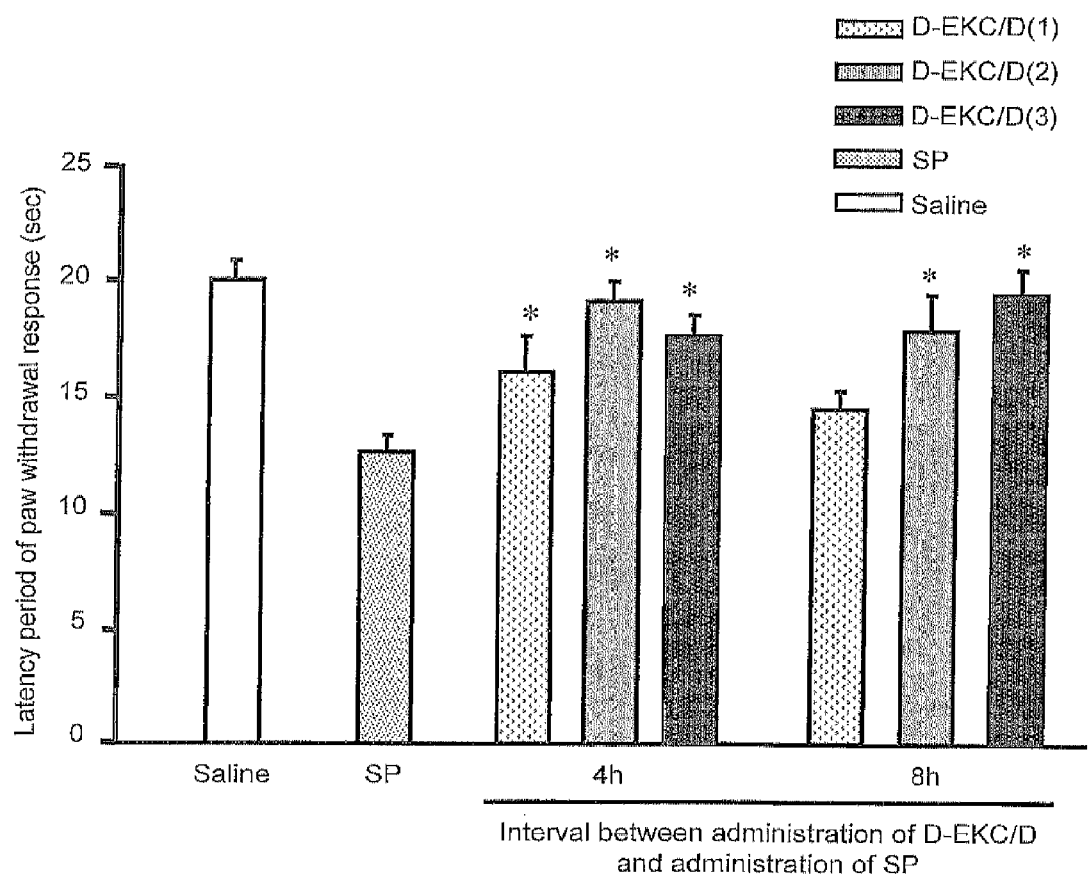
FIG. 7 shows the suppressive effects of D-EKC/D (1)-(3) on SP-induced thermal hyperalgesia.

The results are shown in FIG. 7. The latency period following noxious thermal stimulation in rats after intrathecal administration of saline was about 20 seconds (Saline). Similarly, the latency period after administration of $10^{-6}$M (10 pmol/10 µl) SP was about 13 seconds (SP). Hence, SP was administered at 4 hours after intrathecal administration of D-EKC/D (1), (2), or (3), so that the latency period following administration of SP was significantly attenuated by preadministration of D-EKC/D (1), (2), or (3). However, with the interval between the administration of D-EKC/D (1), (2), or (3) and SP of 8 hours, significant attenuation of the latency period was observed in the case of preadministration of D-EKC/D (2) and (3) alone. It was thus confirmed that D-EKC/D (1) differs from D-EKC/D (2) and (3) in duration of effectiveness.

Example 5

Analgesic Effects of Peptides with Amino Acid Deleted from the N-Terminus

In this experiment, the effects of intrathecal preadministration of D-EKC/D (3), (5), or (7) and Spantide I on pain behavior following intraplantar administration of formalin were confirmed.

In Example 5, $10^{-3}$M (10 nmol/10 µl) D-EKC/D (3), (5), or (7), Spantide I, or saline (10 µl) was administered to intrathecally catheterized rats via catheters and then 4 hours later, 50 µl of 2% formalin was administered subcutaneously to hind paws of rats. The number of flinching (pain behavior) was determined for 60 minutes after formalin administration, so that the degree of pain could be evaluated. During the 10-minute period after formalin administration (referred to as phase I), pain behavior was measured once every 2 minutes (1 minute per measurement). During the period from 10 minutes to 60 minutes after formalin administration (referred to as phase II), pain behavior was measured once every 5 minutes (1 minute per measurement), so that the degree of pain could be evaluated. During phase I, behavior (phasic pain) resulting from chemical stimulation accompanying formalin administration was observed. During phase II, tonic pain following the phasic pain was observed.

Figure 8A:
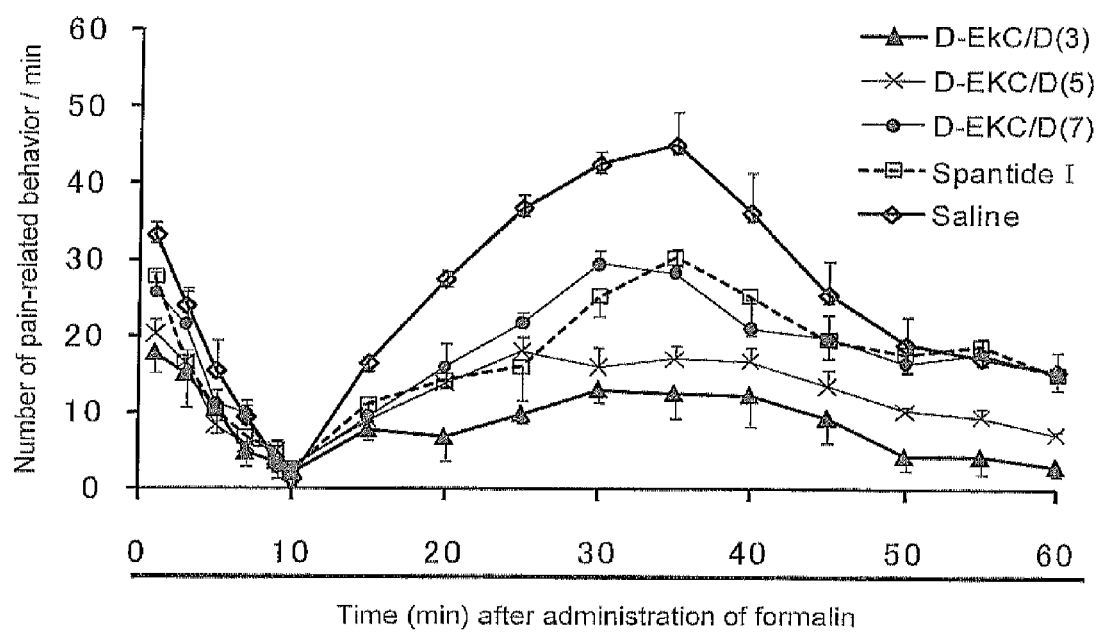
FIG. 8A shows analgesic effects of D-EKC/D (3), D-EKC/D (5), and D-EKC/D (7).
Figure 8B:
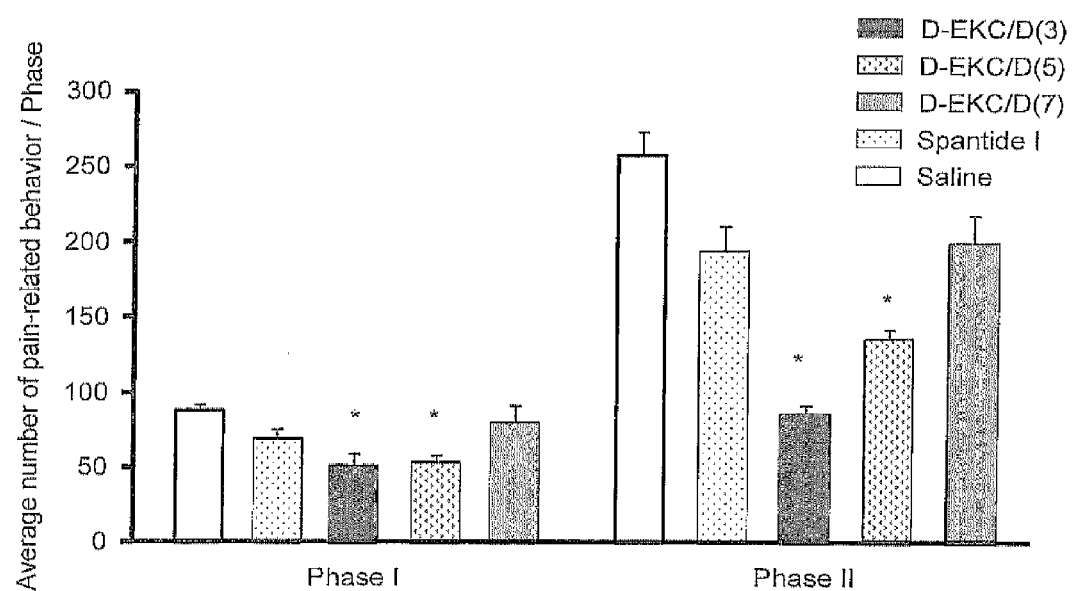
FIG. 8B shows analgesic effects of D-EKC/D (3), D-EKC/D (5), and D-EKC/D (7).

FIG. 8A shows the results. The horizontal axis indicates time (minutes) after formalin administration and the vertical axis indicates the measured number of pain behavior per minute. FIG. 8B shows the average numbers of pain behavior determined during phase I and phase II.

It was confirmed for both D-EKC/D (3) and D-EKC/D (5) that the numbers of pain behavior significantly decreased during both phase I and phase II. It was thus confirmed that suppressing effects of D-EKC/D (3) and D-EKC/D (5) on formalin-induced pain behavior were sustained longer compared with the effects of Spantide I.

Example 6

Anti-Inflammatory Effects of Peptides with Amino Acids Deleted from the N-Terminus In Example 6, $10^{-3}$M (10 nmol/10 µl) D-EKC/D (3), (5), or (7), Spantide I, or saline (10 µl) was administered to intrathecally catheterized rats via catheters. Four hours later, 100 µl of 2% carrageenan (2 mg/100 µl) was subcutaneously administered to rat plantar.

Paw size was measured with time for 60 minutes after carrageenan administration. The paw size (control) before carrageenan administration was designated as the basal level, and the increases in paw size were then calculated.

Meanwhile, noxious thermal stimulation was applied to paw plantar using infrared rays at 10-minute intervals after carrageenan administration. The time (latency period) required for withdrawal response to take place was measured. The latency period before untreated rats following noxious thermal stimulation was designated as the control latency period.

Figure 9A:
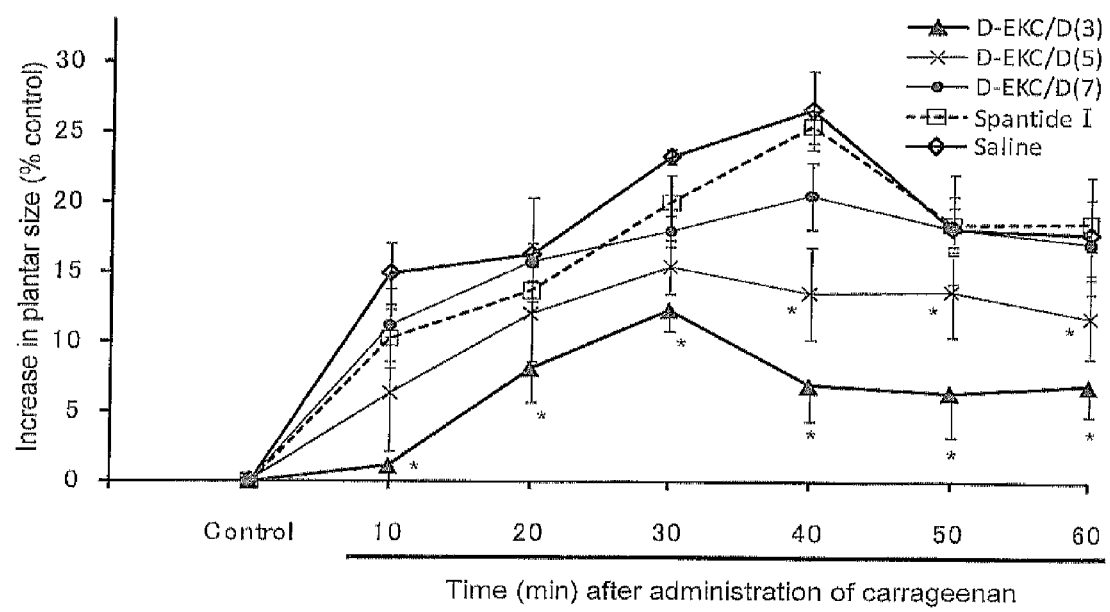
FIG. 9A shows anti-inflammatory effects of D-EKC/D (3), D-EKC/D (5), and D-EKC/D (7).
Figure 9B:
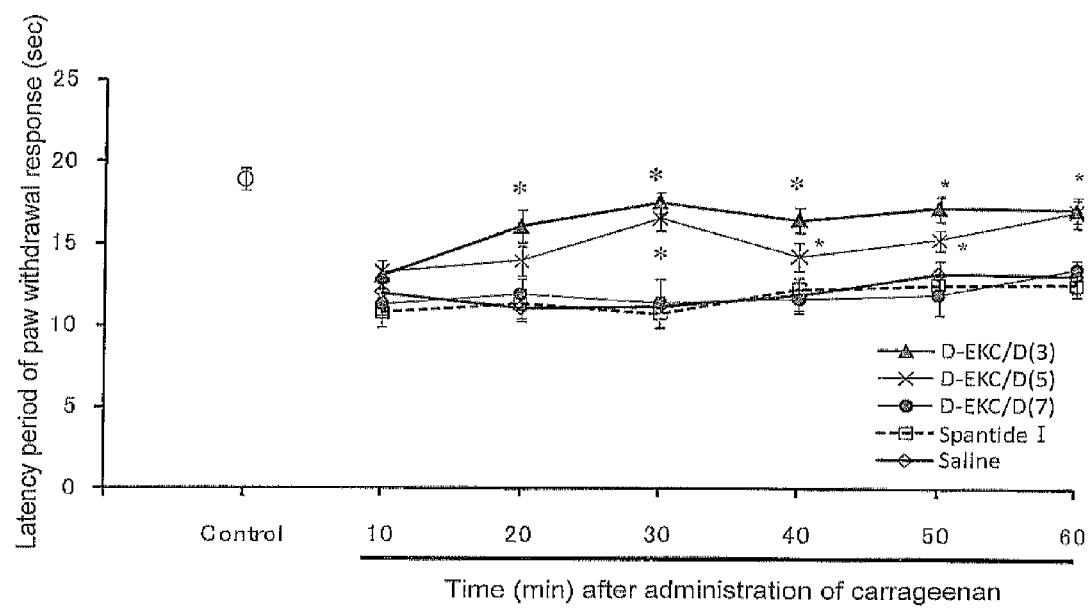
FIG. 9B shows the suppressive effects of D-EKC/D (3), D-EKC/D (5), and D-EKC/D (7) on SP-induced thermal hyperalgesia.

The time course changes of increases in paw size is shown in FIG. 9A. The time course changes of the time required for withdrawal response to take place are shown in FIG. 9B. It was confirmed for D-EKC/D (3) and D-EKC/D (5) that significant decreases in the rate of increase of paw sizes and significant increases in withdrawal time were confirmed. It was thus confirmed that the effects of D-EKC/D (3) and D-EKC/D (5) were sustained to a greater extent than the effects of Spantide I.

Example 7

Anti-Inflammatory Effects of Peptides with Amino Acids Deleted from the N-Terminus (2)

Experiment A

100 µl of saline or $10^{-3}$M (100 nmol/100 D-EKC/D (3) was subcutaneously administered to rat plantar. Paw size was measured with time for 60 minutes after administration. Paw size (control) before administration was designated as the basal level, and increases in paw size were then calculated.

Figure 10A:
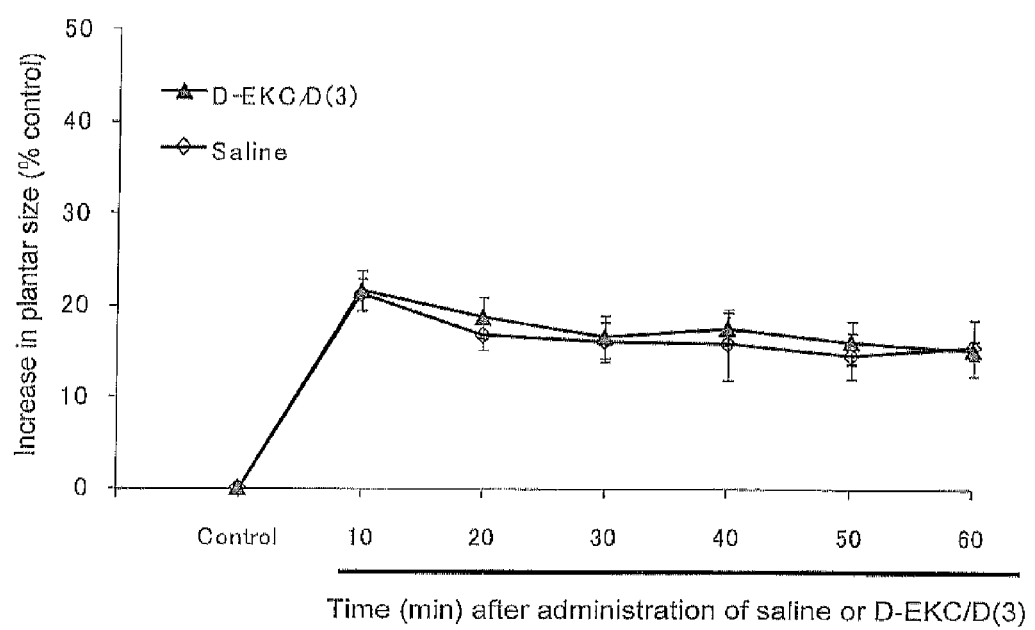
FIG. 10A shows the result in which no inflammation had been caused by subcutaneous administration of D-EKC/D (3) to plantar.

The results are shown in FIG. 10A. In the ease of administration of D-EKC/D (3) alone, the paw plantar size tentatively increased, but at 60 minutes after administration, the paw plantar size had been restored to near the basal (control) level. Specifically, it was confirmed that no inflammation reaction took place even when the peptide was administered.

Experiment B

100 μl of saline, $10^{-3}$M (100 nmol/100 μl) D-EKC/D (3), or $10^{-3}$M (100 nmol/100 μl) Spantide II ($N^6$-[(3-pyridinyl)carbonyl]-D-Lys-L-Pro-3-(3-pyridinyl)-L-Ala-L-Pro-3,4-dichloro-D-Phe-L-Asn-D-Trp-L-Phe-D-Trp-L-Leu-L-Nle-$NH_2$) (SEQ ID NO: 21) was subcutaneously administered to rat plantar. Four (4) hours later, 100 μl (2 mg/100 μl) of 2% carrageenan was subcutaneously administered to rat plantar. Paw size was measured every 10 minutes for 60 minutes after carrageenan administration. The paw size (control) before carrageenan administration was designated as the basal level and increases in paw size were then calculated.

Figure 10B:
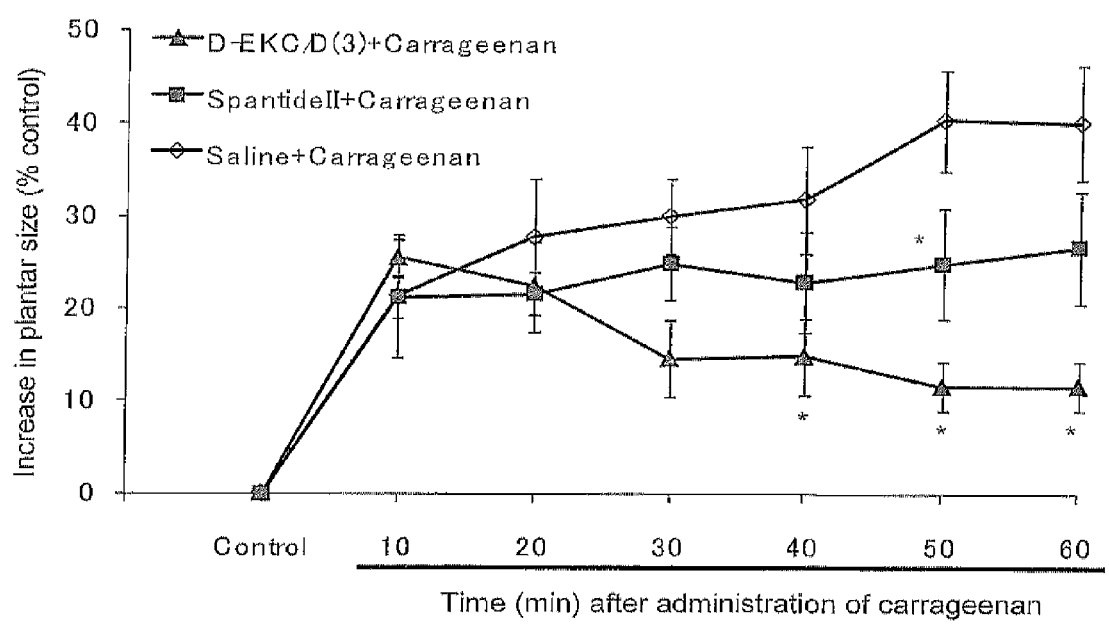
FIG. 10B shows anti-inflammatory effects of D-EKC/D (3).

The results are shown in FIG. 10B. Administration of D-EKC/D (3) suppressed increases in paw size accompanying carrageenan-induced inflammation more significantly than administration of Spantide II.

Experiment C

Procedures similar to those in Experiment B were performed, except for administration of carrageenan at 8 hours after administration of saline, D-EKC/D (3), or Spantide II.

Figure 10C:
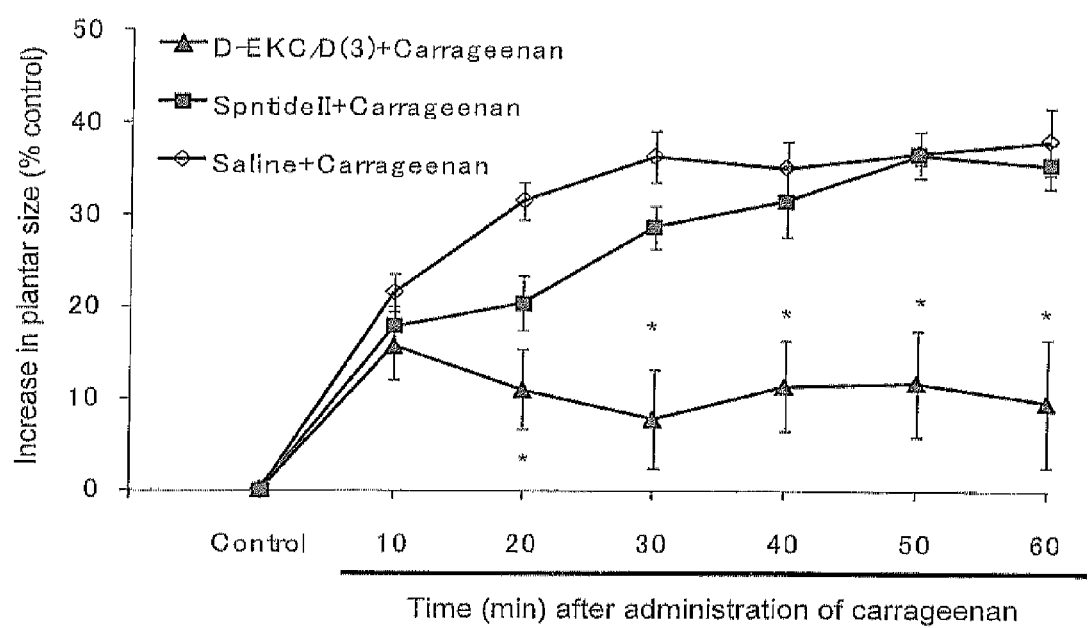
FIG. 10C shows anti-inflammatory effects of D-EKC/D (3).

The results are shown in FIG. 10C. Administration of D-EKC/D (3) suppressed increases in paw size accompanying carrageenan-induced inflammation. No suppressive effects due to Spantide II administration were confirmed.

Experiment D

Procedures similar to those in Experiment B were performed except that the test with Spantide II was not conducted and carrageenan was administered at 14 hours after administration of saline or D-EKC/D (3).

Figure 10D:
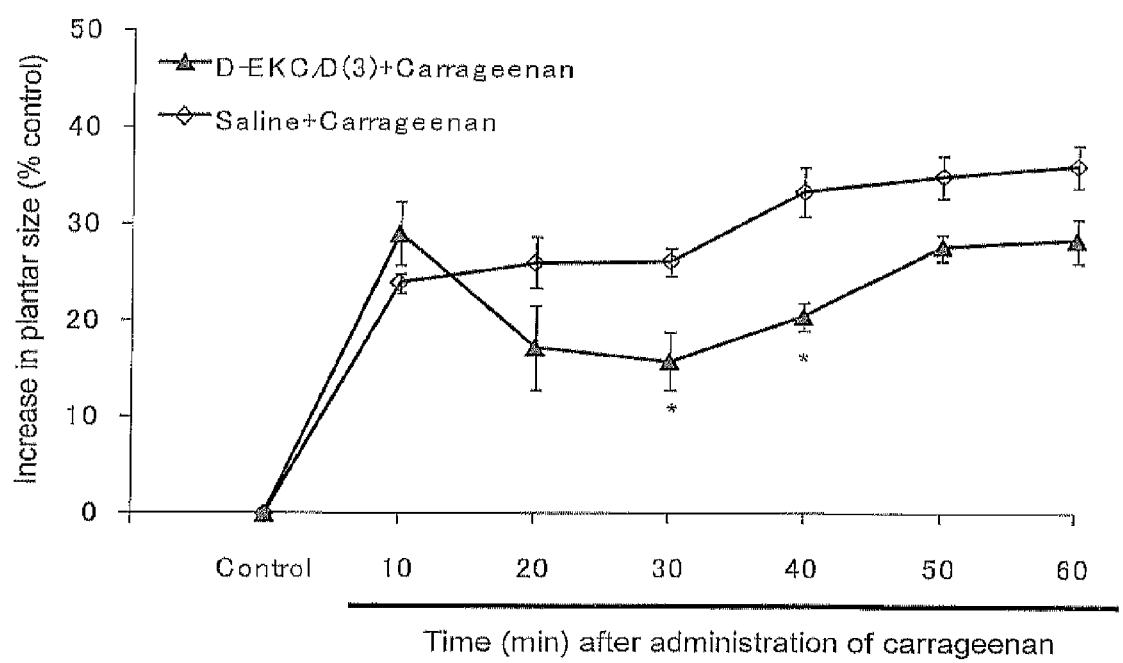
FIG. 10D shows anti-inflammatory effects of D-EKC/D (3).

In addition, Spantide II was not used in this experiment, since the cessation of the effects of Spantide II was observed in Experiment C. The results are shown in FIG. 10D. Administration of D-EKC/D (3) suppressed increases in paw size accompanying carrageenan-induced inflammation.

All publications, patents, and patent applications cited in this description are herein incorporated by reference in their entirety.

SEQUENCE LISTING FREE TEXT

SEQ ID NO: 1:
Amidation
SEQ ID NO: 2:
Synthetic peptide
Xaa denotes D-tryptophan.
Xaa denotes D-tryptophan.
Amidation
SEQ ID NO: 3:
Synthetic peptide
Xaa denotes D-tryptophan.
Amidation
SEQ ID NO: 4:
Synthetic peptide
Xaa denotes D-tryptophan.
Amidation
SEQ ID NO: 5:
Synthetic peptide
Xaa denotes D-tryptophan.
Amidation
SEQ ID NO: 6:
Synthetic peptide
Xaa denotes D-tryptophan.
Amidation
SEQ ID NO: 7:
Synthetic peptide
Xaa denotes D-tryptophan.
Amidation
SEQ ID NO: 8:
Synthetic peptide
Xaa denotes D-tryptophan.
Amidation
SEQ ID NO: 9:
Synthetic peptide
Xaa denotes D-tryptophan.
Amidation
SEQ ID NO: 10:
Amidation
SEQ ID NO: 11:
Synthetic peptide
Xaa denotes D-arginine.
Xaa denotes D-phenylalanine.
Xaa denotes D-tryptophan.
Xaa denotes D-tryptophan.
Amidation
SEQ ID NO: 12:
Synthetic peptide
Xaa denotes D-arginine.
Xaa denotes D-tryptophan.
Xaa denotes D-tryptophan.
Amidation
SEQ ID NO: 13:
Synthetic peptide
Xaa denotes D-tryptophan.
Amidation
SEQ ID NO: 14:
Synthetic peptide
Xaa denotes D-tryptophan.
Amidation
SEQ ID NO: 15:
Synthetic peptide
Xaa denotes D-tryptophan.
Amidation
SEQ ID NO: 16:
Synthetic peptide
Xaa denotes D-tryptophan.
Amidation
SEQ ID NO: 17:
Synthetic peptide
Xaa denotes D-tryptophan.
Amidation
SEQ ID NO: 18:
Synthetic peptide
Xaa denotes D-tryptophan.
Amidation
SEQ ID NO: 19:
Synthetic peptide
Xaa denotes D-tryptophan.
Amidation
SEQ ID NO: 20:
Synthetic peptide
Xaa denotes D-tryptophan.
Amidation
SEQ ID NO: 21:
Synthetic peptide
Xaa denotes $N^6$-[(3-pyridinyl)carbonyl]-D-Lys.
Xaa denotes 3-(3-pyridinyl)-L-Ala.
Xaa denotes 3,4-dichloro-D-Phe.
Xaa denotes D-tryptophan.
Xaa denotes D-tryptophan.
Xaa denotes Nle
Amidation
Sequence Listing
PH-4379PCT Sequence Listing.txt .

The invention claimed is:

1. A peptide selected from the group consisting of:
   (a) an amino acid sequence represented by Ala-Tyr-Gln-Leu-Glu-His-Thr-Phe-Gln-DTrp-Leu-Leu-NH$_2$ (SEQ ID NO: 4);
   (b) a partial sequence of SEQ ID NO: 4 consisting of 6 to 11 consecutive amino acids including at least the C-terminal Thr-Phe-Gln-DTrp-Leu-Leu-NH$_2$ (SEQ ID NO: 8); and
   (c) an amino acid sequence consisting of sequence (a) or (b), modified with either a deletion of a single amino acid, a substitution of a single amino acid, or an addition of from 1 to 5 amino acids at a position other than DTrp and C-terminal Leu-NH$_2$, wherein the modified amino acid sequence of (a) or (b) excludes an amino acid sequence where Phe is substituted with DTrp.

2. The peptide according to claim 1, wherein the peptide is sequence (a) or (b).

3. A method for suppressing substance P activity in vitro or in vivo, comprising the step of contacting substance P in vitro or in vivo with the peptide according to claim 1.

4. A method for treatment of pain, comprising the step of administering to a subject that requires pain treatment an effective dose of the peptide according to claim 1.

5. A method for treatment of inflammation, comprising the step of administering to a subject that requires treatment of inflammation an effective dose of the peptide according to claim 1.

6. A method for treatment of itch, comprising the step of administering to a subject that requires treatment of itch an effective dose of the peptide according to claim 1.

7. A pharmaceutical composition, comprising the peptide according to claim 1, and at least one pharmaceutically acceptable carrier, or an excipient.

* * * * *

SEQUENCE LISTING

<160> NUMBER OF SEQ ID NOS: 23

<210> SEQ ID NO 1
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: AMIDATION

<400> SEQUENCE: 1

Ala Tyr Gln Leu Glu His Thr Phe Gln Gly Leu Leu
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is the D-form of tryptophan
<220> FEATURE:
<221> NAME/KEY: misc_feature
<222> LOCATION: (10)..(10)
<223> OTHER INFORMATION: Xaa is the D-form of tryptophan
<220> FEATURE:
<221> NAME/KEY: MOD_RES
<222> LOCATION: (12)..(12)
<223> OTHER INFORMATION: AMIDATION

<400> SEQUENCE: 2

Ala Tyr Gln Leu Glu His Thr Xaa Gln Xaa Leu Leu
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is the D-form of tryptophan
<220> FEATURE:
<221> NAME/KEY: MOD_RES
<222> LOCATION: (12)..(12)
<223> OTHER INFORMATION: AMIDATION

<400> SEQUENCE: 3

Ala Tyr Gln Leu Glu His Thr Xaa Gln Gly Leu Leu
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (10)..(10)
<223> OTHER INFORMATION: Xaa is the D-form of tryptophan
<220> FEATURE:
<221> NAME/KEY: MOD_RES
<222> LOCATION: (12)..(12)
<223> OTHER INFORMATION: AMIDATION

```
<400> SEQUENCE: 4

Ala Tyr Gln Leu Glu His Thr Phe Gln Xaa Leu Leu
1               5                   10

<210> SEQ ID NO 5
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa is the D-form of tryptophan
<220> FEATURE:
<221> NAME/KEY: MOD_RES
<222> LOCATION: (9)..(9)
<223> OTHER INFORMATION: AMIDATION

<400> SEQUENCE: 5

Leu Glu His Thr Phe Gln Xaa Leu Leu
1               5

<210> SEQ ID NO 6
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is the D-form of tryptophan
<220> FEATURE:
<221> NAME/KEY: MOD_RES
<222> LOCATION: (8)..(8)
<223> OTHER INFORMATION: AMIDATION

<400> SEQUENCE: 6

Glu His Thr Phe Gln Xaa Leu Leu
1               5

<210> SEQ ID NO 7
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa is the D-form of tryptophan
<220> FEATURE:
<221> NAME/KEY: MOD_RES
<222> LOCATION: (7)..(7)
<223> OTHER INFORMATION: AMIDATION

<400> SEQUENCE: 7

His Thr Phe Gln Xaa Leu Leu
1               5

<210> SEQ ID NO 8
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is the D-form of tryptophan
```

```
<220> FEATURE:
<221> NAME/KEY: MOD_RES
<222> LOCATION: (6)..(6)
<223> OTHER INFORMATION: AMIDATION

<400> SEQUENCE: 8

Thr Phe Gln Xaa Leu Leu
1               5

<210> SEQ ID NO 9
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is the D-form of tryptophan
<220> FEATURE:
<221> NAME/KEY: MOD_RES
<222> LOCATION: (5)..(5)
<223> OTHER INFORMATION: AMIDATION

<400> SEQUENCE: 9

Phe Gln Xaa Leu Leu
1               5

<210> SEQ ID NO 10
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 10

Arg Pro Lys Pro Gln Gln Phe Phe Gly Leu Met
1               5                   10

<210> SEQ ID NO 11
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is the D-form of arginine
<220> FEATURE:
<221> NAME/KEY: misc_feature
<222> LOCATION: (5)..(5)
<223> OTHER INFORMATION: Xaa is the D-form of phenylalanine
<220> FEATURE:
<221> NAME/KEY: misc_feature
<222> LOCATION: (7)..(7)
<223> OTHER INFORMATION: Xaa is the D-form of tryptophan
<220> FEATURE:
<221> NAME/KEY: misc_feature
<222> LOCATION: (9)..(9)
<223> OTHER INFORMATION: Xaa is the D-form of tryptophan
<220> FEATURE:
<221> NAME/KEY: MOD_RES
<222> LOCATION: (11)..(11)
<223> OTHER INFORMATION: AMIDATION

<400> SEQUENCE: 11

Xaa Pro Lys Pro Xaa Gln Xaa Phe Xaa Leu Leu
1               5                   10
```

```
<210> SEQ ID NO 12
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is the D-form of arginine
<220> FEATURE:
<221> NAME/KEY: misc_feature
<222> LOCATION: (7)..(7)
<223> OTHER INFORMATION: Xaa is the D-form of tryptophan
<220> FEATURE:
<221> NAME/KEY: misc_feature
<222> LOCATION: (9)..(9)
<223> OTHER INFORMATION: Xaa is the D-form of tryptophan
<220> FEATURE:
<221> NAME/KEY: MOD_RES
<222> LOCATION: (11)..(11)
<223> OTHER INFORMATION: AMIDATION

<400> SEQUENCE: 12

Xaa Pro Lys Pro Gln Gln Xaa Phe Xaa Leu Leu
1               5                   10

<210> SEQ ID NO 13
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa is the D-form of tryptophan
<220> FEATURE:
<221> NAME/KEY: MOD_RES
<222> LOCATION: (11)..(11)
<223> OTHER INFORMATION: AMIDATION

<400> SEQUENCE: 13

Tyr Gln Leu Glu His Thr Xaa Gln Gly Leu Leu
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa is the D-form of tryptophan
<220> FEATURE:
<221> NAME/KEY: MOD_RES
<222> LOCATION: (10)..(10)
<223> OTHER INFORMATION: AMIDATION

<400> SEQUENCE: 14

Gln Leu Glu His Thr Xaa Gln Gly Leu Leu
1               5                   10

<210> SEQ ID NO 15
<211> LENGTH: 9
<212> TYPE: PRT
<213> ORGANISM: Artificial
<220> FEATURE:
<223> OTHER INFORMATION: Synthetic peptide
<220> FEATURE:
```

```
<221> NAME/KEY: misc_feature
<222> LOCATION: (5)..(5)
<223> OTHER INFORMATION: Xaa is the D-form of tryptophan
<220> FEATURE:
<221> NAME/KEY: MOD_RES
<222> LOCATION: (9)..(9)
<223> OTHER INFORMATION: AMIDATION

<400> SEQUENCE: 15

Leu Glu His Thr Xaa Gln Gly Leu Leu
1               5

<210> SEQ ID NO 16
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa is the D-form of tryptophan
<220> FEATURE:
<221> NAME/KEY: MOD_RES
<222> LOCATION: (8)..(8)
<223> OTHER INFORMATION: AMIDATION

<400> SEQUENCE: 16

Glu His Thr Xaa Gln Gly Leu Leu
1               5

<210> SEQ ID NO 17
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is the D-form of tryptophan
<220> FEATURE:
<221> NAME/KEY: MOD_RES
<222> LOCATION: (7)..(7)
<223> OTHER INFORMATION: AMIDATION

<400> SEQUENCE: 17

His Thr Xaa Gln Gly Leu Leu
1               5

<210> SEQ ID NO 18
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is the D-form of tryptophan
<220> FEATURE:
<221> NAME/KEY: MOD_RES
<222> LOCATION: (6)..(6)
<223> OTHER INFORMATION: AMIDATION

<400> SEQUENCE: 18

Thr Xaa Gln Gly Leu Leu
1               5

<210> SEQ ID NO 19
<211> LENGTH: 11
```

```
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa is the D-form of tryptophan
<220> FEATURE:
<221> NAME/KEY: MOD_RES
<222> LOCATION: (11)..(11)
<223> OTHER INFORMATION: AMIDATION

<400> SEQUENCE: 19

Tyr Gln Leu Glu His Thr Phe Gln Xaa Leu Leu
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is the D-form of tryptophan
<220> FEATURE:
<221> NAME/KEY: MOD_RES
<222> LOCATION: (10)..(10)
<223> OTHER INFORMATION: AMIDATION

<400> SEQUENCE: 20

Gln Leu Glu His Thr Phe Gln Xaa Leu Leu
1               5                   10

<210> SEQ ID NO 21
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N6-[(3-Pyridinyl)carbonyl]-D-Lys
<220> FEATURE:
<221> NAME/KEY: misc_feature
<222> LOCATION: (3)..(3)
<223> OTHER INFORMATION: Xaa is 3-(3-pyridinyl)-L-Ala
<220> FEATURE:
<221> NAME/KEY: misc_feature
<222> LOCATION: (5)..(5)
<223> OTHER INFORMATION: Xaa is 3,4-dichloro-D-Phe
<220> FEATURE:
<221> NAME/KEY: misc_feature
<222> LOCATION: (7)..(7)
<223> OTHER INFORMATION: Xaa is the D-form of tryptophan
<220> FEATURE:
<221> NAME/KEY: misc_feature
<222> LOCATION: (9)..(9)
<223> OTHER INFORMATION: Xaa is the D-form of tryptophan
<220> FEATURE:
<221> NAME/KEY: misc_feature
<222> LOCATION: (11)..(11)
<223> OTHER INFORMATION: Xaa is Nle
<220> FEATURE:
<221> NAME/KEY: MOD_RES
<222> LOCATION: (11)..(11)
<223> OTHER INFORMATION: AMIDATION

<400> SEQUENCE: 21

Xaa Pro Xaa Pro Xaa Asn Xaa Phe Xaa Leu Xaa
1               5                   10
```

```
<210> SEQ ID NO 22
<211> LENGTH: 5
<212> TYPE: PRT
<213> ORGANISM: Artificial sequence
<220> FEATURE:
<223> OTHER INFORMATION: consensus sequence of animals including
      vertebrate and invertebrate
<220> FEATURE:
<221> NAME/KEY: misc_feature
<222> LOCATION: (2)..(2)
<223> OTHER INFORMATION: Xaa is any hydrophobic amino acid
<220> FEATURE:
<221> NAME/KEY: MOD_RES
<222> LOCATION: (5)..(5)
<223> OTHER INFORMATION: AMIDATION

<400> SEQUENCE: 22

Phe Xaa Gly Leu Met
1               5

<210> SEQ ID NO 23
<211> LENGTH: 5
<212> TYPE: PRT
<213> ORGANISM: Artificial sequence
<220> FEATURE:
<223> OTHER INFORMATION: consensus sequence of animals including
      vertebrate and invertebrate
<220> FEATURE:
<221> NAME/KEY: misc_feature
<222> LOCATION: (2)..(2)
<223> OTHER INFORMATION: Xaa is any hydrophobic amino acid
<220> FEATURE:
<221> NAME/KEY: MOD_RES
<222> LOCATION: (5)..(5)
<223> OTHER INFORMATION: AMIDATION

<400> SEQUENCE: 23

Phe Xaa Gly Leu Leu
1               5
```